US010398595B2

(12) United States Patent
Zacharias

(10) Patent No.: US 10,398,595 B2
(45) Date of Patent: Sep. 3, 2019

(54) CYCLIC APERTURE FLOW REGULATOR SYSTEM

(71) Applicant: Novartis AG, Basel (CH)

(72) Inventor: Jaime Zacharias, Santiago (CL)

(73) Assignee: Novartis AG, Basel (CH)

( * ) Notice: Subject to any disclaimer, the term of this patent is extended or adjusted under 35 U.S.C. 154(b) by 100 days.

(21) Appl. No.: 14/891,916

(22) PCT Filed: Jun. 16, 2014

(86) PCT No.: PCT/IB2014/062252
§ 371 (c)(1),
(2) Date: Nov. 17, 2015

(87) PCT Pub. No.: WO2014/195927
PCT Pub. Date: Dec. 11, 2014

(65) Prior Publication Data
US 2016/0128869 A1    May 12, 2016

Related U.S. Application Data

(60) Provisional application No. 61/897,827, filed on Oct. 31, 2013, provisional application No. 61/830,792, filed on Jun. 4, 2013.

(51) Int. Cl.
*A61F 9/007*    (2006.01)
*A61M 1/00*    (2006.01)

(52) U.S. Cl.
CPC .......... *A61F 9/00736* (2013.01); *A61F 9/007* (2013.01); *A61M 1/0035* (2014.02);
(Continued)

(58) Field of Classification Search
CPC .. A61F 9/00736; A61F 9/007; A61F 9/00745; A61M 1/0035; A61M 1/0082;
(Continued)

(56) References Cited

U.S. PATENT DOCUMENTS 4,770,654 A * 9/1988 Rogers ................ A61F 9/00736
604/22
5,569,188 A    10/1996 Mackool
(Continued)

FOREIGN PATENT DOCUMENTS

CN    1703251 A    11/2005
CN    101426541 A    5/2009
(Continued)

OTHER PUBLICATIONS

International Searching Authority, International Preliminary Report on Patentability, PCT/IB2014/062252, dated Dec. 8, 2015, 8 pages.
(Continued)

*Primary Examiner* — Kevin C Sirmons
*Assistant Examiner* — Tezita Z Watts

(57) ABSTRACT

A cyclic aperture flow regulator system has an adjustable fluid aperture in a fluid path connecting the aspiration port of a surgical probe with a vacuum source. The cross-sectional area of the fluid aperture can be modified by an actuator. The actuator is controlled to modify the cross-sectional area of the adjustable fluid aperture in cycles. During each cycle, the fluid aperture cross-sectional area is substantially reduced or closed. The cycles occur at a rate fast enough to produce a substantially steady flow, with minimum flow ripple and pressure ripple.

16 Claims, 27 Drawing Sheets

(52) U.S. Cl.
CPC ........ *A61M 1/0037* (2013.01); *A61M 1/0066* (2013.01); *A61M 1/0082* (2014.02); *A61F 9/00745* (2013.01); *A61M 2210/0612* (2013.01)

(58) Field of Classification Search
CPC .............. A61M 1/0037; A61M 1/0066; A61M 1/0039; A61M 1/0047; A61M 1/0064; A61M 2210/0612; A61M 1/0041; A61M 1/0043; A61M 1/0045; F16K 3/267
See application file for complete search history.

(56) References Cited

U.S. PATENT DOCUMENTS

| | | | | |
|---|---|---|---|---|
| 5,713,850 | A * | 2/1998 | Heilmann | A61M 1/285 |
| | | | | 137/625.46 |
| 2002/0166989 | A1* | 11/2002 | Peterson | A61M 1/1656 |
| | | | | 251/208 |
| 2006/0129092 | A1* | 6/2006 | Hanlon | A61M 39/12 |
| | | | | 604/93.01 |
| 2007/0088282 | A1* | 4/2007 | Ranalletta | A61M 5/204 |
| | | | | 604/184 |
| 2007/0270744 | A1* | 11/2007 | Dacquay | A61F 9/0017 |
| | | | | 604/114 |
| 2013/0053693 | A1* | 2/2013 | Breznock | A61M 1/3627 |
| | | | | 600/433 |
| 2013/0060210 | A1* | 3/2013 | Ross | A61M 1/0035 |
| | | | | 604/318 |

FOREIGN PATENT DOCUMENTS

| | | |
|---|---|---|
| CN | 102245140 A | 11/2011 |
| CN | 102361606 A | 2/2012 |
| GB | 2427142 A | 12/2006 |
| TW | 243411 B | 3/1995 |
| WO | 9632144 A1 | 10/1996 |
| WO | 2006134326 | 12/2006 |

OTHER PUBLICATIONS

International Searching Authority, International Search Report, PCT/IB2014/062252, dated Sep. 22, 2014, 4 pages.

* cited by examiner

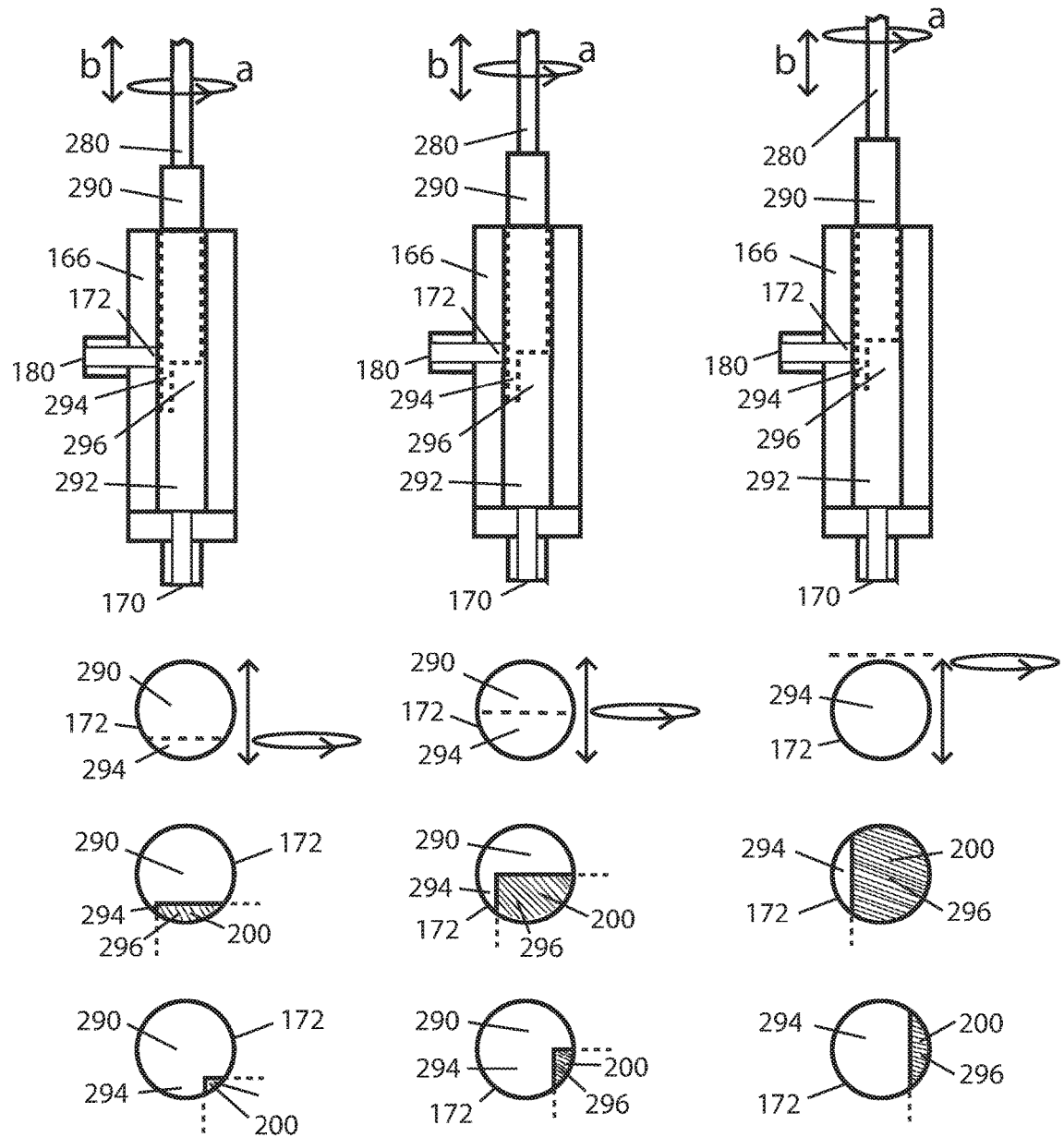

DETAIL B

DETAIL C

DETAIL D

DETAIL E

DETAIL F

SECTION D-D

DETAIL G

SECTION C-C

SLICE DETAIL G-1

SLICE DETAIL G-2

SLICE DETAIL G-3

SECTION H-H

SECTION U-U

SECTION P-P

SECTION U-U

SECTION T-T

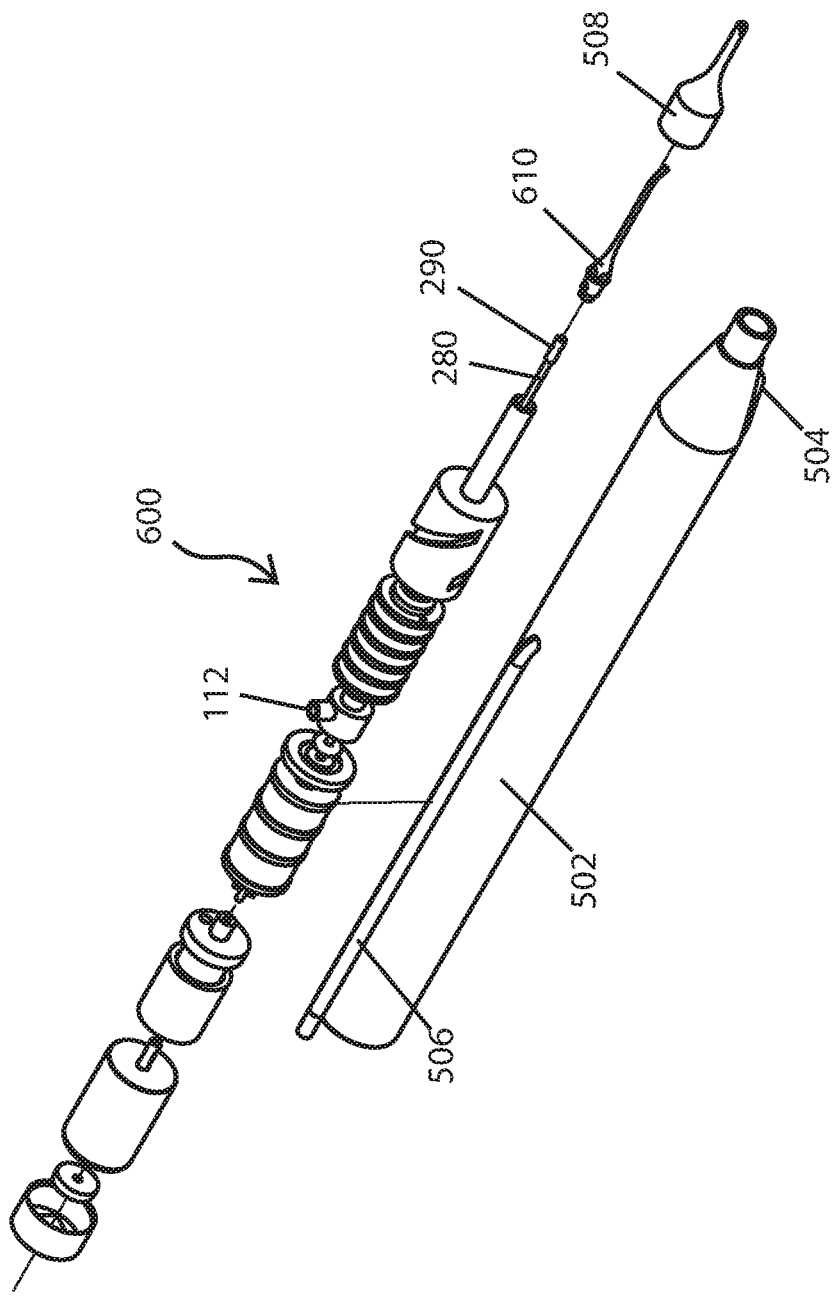

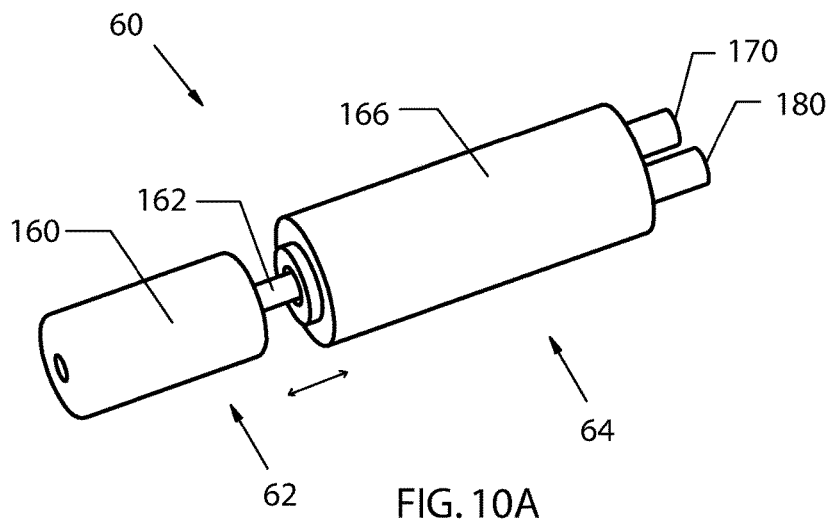
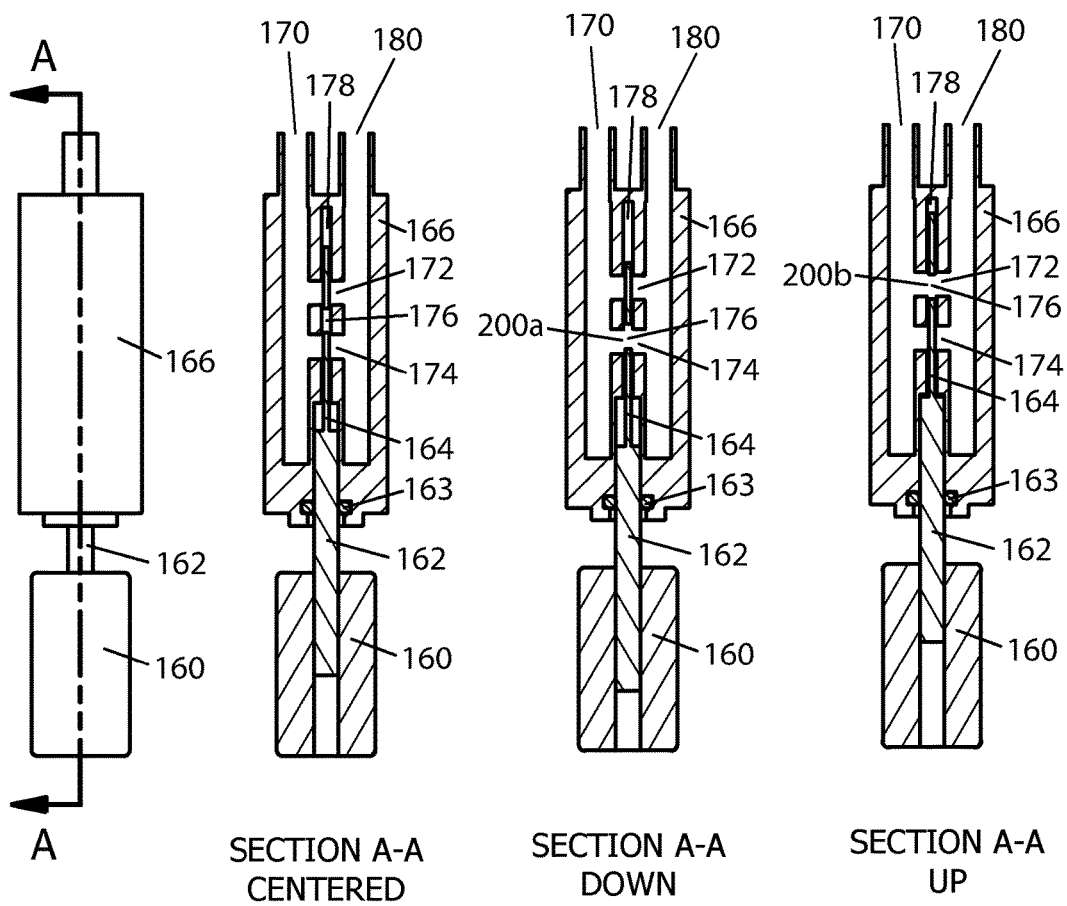
FIG. 10A
SECTION A-A CENTERED
SECTION A-A DOWN
SECTION A-A UP
FIG. 10B  FIG. 10C  FIG. 10D  FIG. 10E

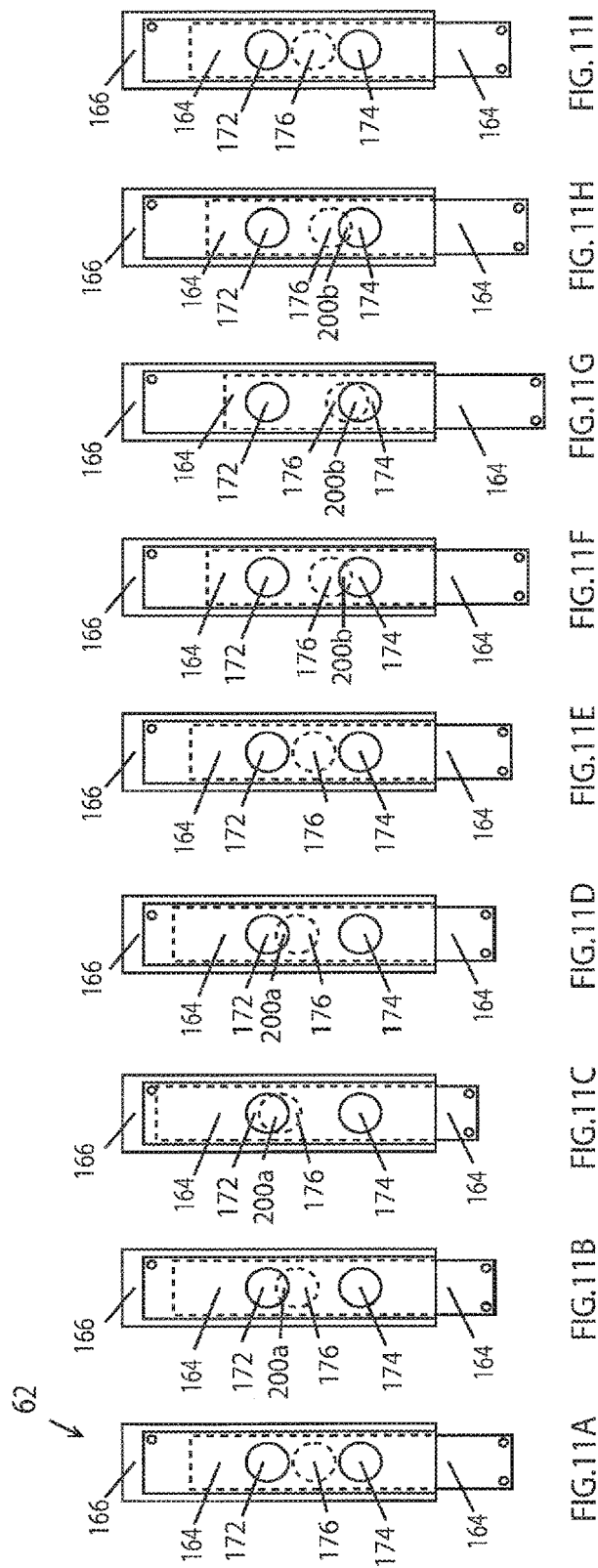

DETAIL F (SECTION)

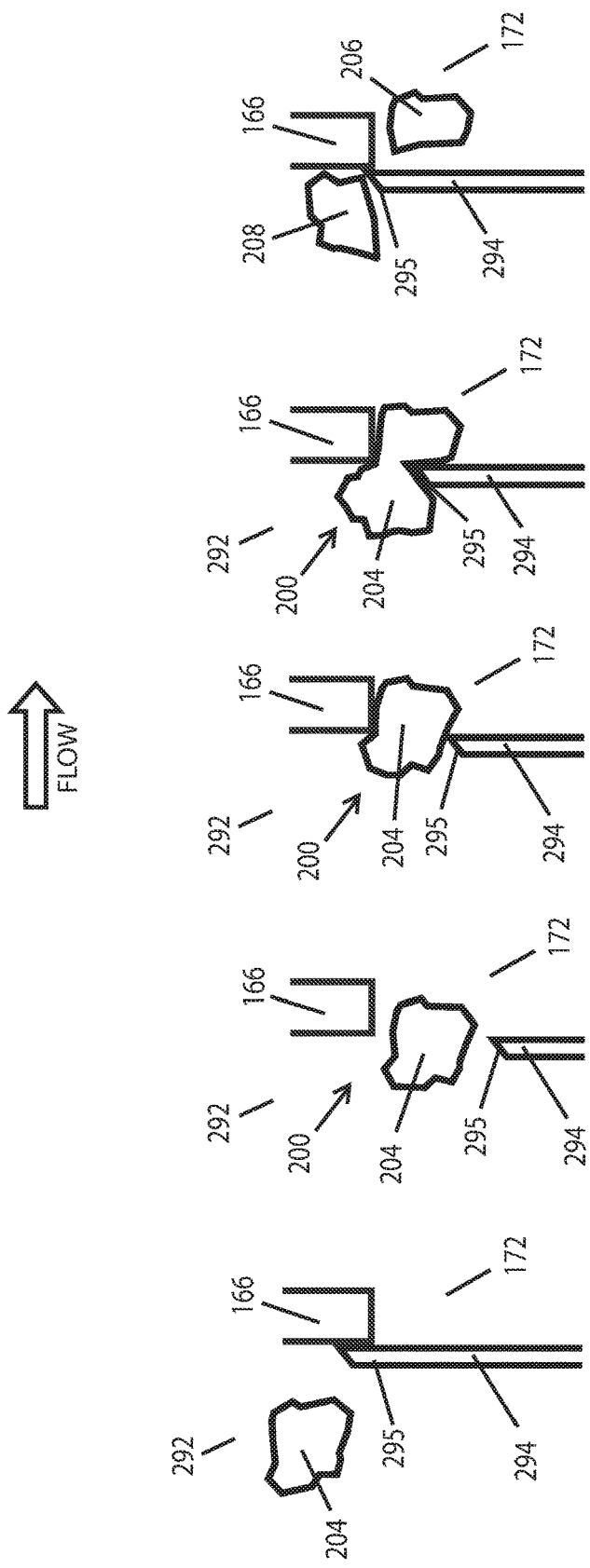

CYCLIC APERTURE FLOW REGULATOR SYSTEM

CROSS REFERENCE TO RELATED APPLICATIONS

This application is a section 371 national phase of International Application No. PCT/IB2014/062252, filed 16 Jun. 2014, titled "CYCLIC APERTURE FLOW REGULATOR SYSTEM.

FIELD OF INVENTION

This invention relates to surgery, specifically to an improved flow regulation system that can be used with advantage in ocular surgery.

BACKGROUND

Various contemporary surgical procedures require aspiration of fluids that may contain solid or semi-solid tissue or other debris. In many cases, the fluids may need to be aspirated from a body cavity such as from within the lens capsule of the eye or a cavity in a joint such as the shoulder or the knee. It is typically desirable to maintain an ambient or a super-ambient pressure within the body cavity during such surgical procedures. For example, the lens of a human eye may develop a cataractous condition that affects a patient's vision. Cataractous lenses are sometimes removed and replaced in a procedure commonly referred to as phacoemulsification. Phacoemulsification procedures are typically performed with an ultrasonically driven surgical probe that is used to break the lens within the lens capsule of the eye. The broken lens is removed through an aspiration line that is coupled to the handpiece and protrudes into the lens capsule. The handpiece has a probe with a tip that is inserted through an incision in the cornea. The handpiece typically contains a number of ultrasonic transducers that convert electrical power into a mechanical oscillating movement of the tip. The distal end of the tip has an opening that is in fluid communication with the aspiration line. The distal end of the tip can also have a sleeve that has an opening in fluid communication with an irrigation line. The irrigation line is typically connected to a pressurized source of fluid that can provide irrigation fluid to the surgical site. The oscillating movement of the tip breaks the lens into small pieces. Lens fragments can also be aspirated without any use of ultrasonic power either using a conventional ultrasonic handpiece or a dedicated aspiration probe that can eventually incorporate an irrigation port, better known as an irrigation/aspiration and the same concerns exist about flow control and vacuum surges described later. The lens pieces and irrigation fluid are drawn into the aspiration line through as aspiration opening on the tip. Phacoemulsification is more likely to be successful if super-ambient pressure can be maintained within the lens capsule and the anterior chamber of the eye during the procedure. However, fluid surges can be created after the distal end of the aspiration line is cleared from momentary obstructions by solid or semi-solid tissue. These fluid surges, also known as post-occlusion surges, can lead to transient aspiration flow rates through opening of the distal end of the surgical probe can transitorily exceed the flow rate through the irrigation line thereby causing eye chamber instability and an eventual collapse of the surrounding tissue. This instability can compromise the safety of the procedure of the eye, with potential undesirable damage to the posterior aspect of the lens capsule of the eye, and/or endothelium cells to be undesirably drawn away from the cornea and towards the distal end the tip of the handpiece. On the other hand, too high an irrigation flow rate may undesirably move endothelium cells away from the cornea, or undesirably cause endothelium cells to be aspirated out of the eye. Conventional phacoemulsification procedures are typically performed using a vacuum pressure of about 350 mmHg. There is a desire to increase the vacuum pressure to assist in aspirating lens fragments faster and with less auxiliary energy such as ultrasound. Lowering the ultrasonic work would be desirable because ultrasound can irritate the eye. Moreover, recent introduction of femtosecond laser assisted cataract surgery (FLACS) allows a laser induced significant softening of the lens material in many cataract procedures, making the use of ultrasonic energy unnecessary, only relying in aspiration of the laser-softened lens tissue material. Consequently, there is a desire to apply vacuums above 500 mmHg to improve the efficacy of aspiration thus reducing the amount of ultrasound delivered inside the eye, or the ability to safely and efficiently aspirate ultrasonically emulsified, laser-softened lens material or primitively soft lens material. However, such higher vacuum exacerbate the surgical risks associated with post-occlusion fluid surges into the surgical probe. Also for example, some orthopedic medical procedures produce particles or other debris that must be removed from a cavity within a joint such as in the shoulder or knee. To remove such particles the surgeon may couple an aspiration tube to the surgical site. The aspiration tube, which pulls the debris from the body, is typically connected to a canister, which is connected to a suction tube connected to wall suction. To ensure that the surgical site is properly distended during surgery, relatively large quantities of irrigation fluid are typically introduced to the body to continuously irrigate the surgical site, and an infusion pump is typically required to offset the high flow created by the hospital vacuum line. The introduction of such amounts of irrigation fluid into the body can cause undesirable or excessive extravasation of irrigation fluid into the surrounding tissue. Also, post-occlusion surges can be created when the suction line is obstructed by solid or semi-solid tissue. Such post-occlusion surges can lead to transient aspiration flow rates through the hospital vacuum line that substantially exceed the flow rate of irrigation fluid and thereby cause a sub-ambient pressure to be momentarily applied to the surrounding tissue. The momentary sub-ambient pressure condition may cause partial collapse of the body cavity, damage to tissue near the distal end of the aspiration tube, and/or undesired tissue or fluid to be drawn towards the distal end of the aspiration tube. Surgical aspiration systems may be designed to allow the surgeon to temporarily reverse the direction of aspiration flow by depressing a reflux switch or bulb attached to the system. The surgeon may do this, for example, if tissue is drawn towards the distal tip of the aspiration tube or handpiece that the surgeon does not desired to be drawn (e.g. tissue that the surgeon does not want to be damaged by the distal tip). The surgeon may also initiate reflux to clear or dislodge an occlusion at the distal tip of the aspiration tube or handpiece. Contemporary post-occlusion surge limiters can limit the vacuum surges within the aspiration system, but only when the vacuum created by the vacuum pump is limited to a level that is safe in consideration of the diameter and length of that surge limiter. For example, considering the typical dimensions of needles and tubing used in ophthalmology, the flow that would be generated by a 500 mmHg vacuum is above 250 cc/min which can undesirably collapse the eye. Therefore, prior art systems that use a Venturi pump must operate modest vacuum levels, e.g. below 300 mmHg unless very small needle bores are used. Such modest vacuum levels significantly limit the available un-occluded flow in such systems. Therefore, such surge limiters are typically not used with peristaltic pumps that will significantly increase the pressure difference in response to an occlusion of the aspiration tip. The absence of pressure rise in response to occlusion in the contemporary aspiration systems limits their ability to aspirate large tissue particles. Also, an in-line surge limiter may reduce the maximum flow rate in the absence of occlusion, even when the surgeon would prefer a higher flow rate to draw certain tissue towards the distal end of the tip (rather than moving the distal end of the tip towards the tissue). Also, an in-line surge limiter can undesirably reduce the maximum reflux flow rate.

Therefore, it would be desirable to provide an aspiration line flow regulator system that maintains a stable ambient or super-ambient pressure within a body cavity during a surgical procedure by limiting vacuum surges in the system.

For example, it would be desirable to provide an aspiration line flow regulator system that is configured such that the flow rate out of the body cavity through the aspiration line does not greatly, or for a prolonged period, exceed the flow rate into the body cavity. In cataract surgery, for example, aspiration flow should be sufficient to quickly engage and aspirate lens particles from the eye, however in the event of an occlusion the high vacuum created in the aspiration line may temporarily produce too high a flow after the occlusion break which could collapse the eye and produce damage.

It would also be desirable to provide an aspiration line flow regulator system that functions safely with limited or reduced flow rate of irrigation fluid through the irrigation line even when using the highest vacuum levels available.

It would also be desirable to provide an aspiration line flow regulator system that can safely take advantage of an aspiration pump that can significantly increase the relative vacuum response to an occlusion.

It would also be desirable to provide an aspiration line flow regulator system that would allow a high aspiration flow rate in the absence of an occlusion, and a reflux feature when commanded by the operator.

It would also be desirable to provide an aspiration line flow regulator system that could allow the use with advantage of the maximum vacuum levels achievable with improved safety and efficacy.

It would also be desired to provide an aspiration line flow regulator system that allows an operator to accurately control the flow rate from a surgical site while maintaining high vacuum levels to, for example, slowly but powerfully aspirate tissue fragments, reducing the need of use of complementary tissue disrupting energies such as ultrasonic emulsification.

SUMMARY

A cyclic aperture flow regulator system is disclosed to prevent post-occlusion instability of a body cavity during surgical aspiration of fluid and tissue fragments through an aspiration opening of a surgical probe. The flow regulator system includes a flow regulator valve portion having a fluid aperture with adjustable cross-sectional area. The flow regulator valve has a valve chamber and a movable member both parts cooperating to define the dimensions of the fluid aperture by the extent of overlap between the movable member and the entrance to fluid passages disposed in the valve chamber. The flow regulator valve portion is inserted in the fluid path connecting the aspiration opening of the surgical probe with a vacuum source. An actuator portion is connected with the flow regulator valve portion and is operable to modify the cross-sectional area of the fluid aperture. A controller provides a command signal to the actuator portion to cause cycles of variation of the cross-sectional area of the fluid aperture with each cycles including at least one segment where the cross-sectional area of the fluid aperture is substantially reduced or eventually closed. The cycles of aperture dimension fluctuation are set to occur at a frequency sufficiently high to produce a substantially steady flow through the surgical probe. Fluid and tissue fragments can be aspirated the body cavity with the surgical probe without instability caused by fluid surges caused by occlusion breaks of the surgical probe aspiration opening. Flow can be regulated by adjusting the vacuum level in the conventional manner. Flow can also be adjusted by modifying the amplitude of the aperture modulation cycles and in this way changing the RMS (root mean square) value of the cross sectional area of the fluid aperture inside the valve portion of the flow regulator system.

BRIEF DESCRIPTION OF THE DRAWINGS

FIGS. 2B to 2D are schematic illustrations of the flow regulator system from FIG. 2A depicting exemplary aperture cross-sections that can occur during operation.

FIG. 8M is an expanded view of a surgical handpiece incorporating an "in-probe" valve portion of the flow regulator system of the present invention.

FIGS. 10A to 10E is a schematic representation of an oscillatory embodiment of the cyclic aperture flow regulator system of the present invention.

FIGS. 11A to 11I is a sequence of illustrations representing the displacement of a movable member having a window along one full cycle of oscillation with respect to a valve body having two fluid passages indicating the cross-sectional area of the resulting fluid aperture on each frame.

FIGS. 16A to 16E are a series of diagrams depicting how particles contained in the fluid can be segmented by the cycling mechanism without impact on overall system operation.

DRAWINGS—REFERENCE NUMERALS

Figure 1A:
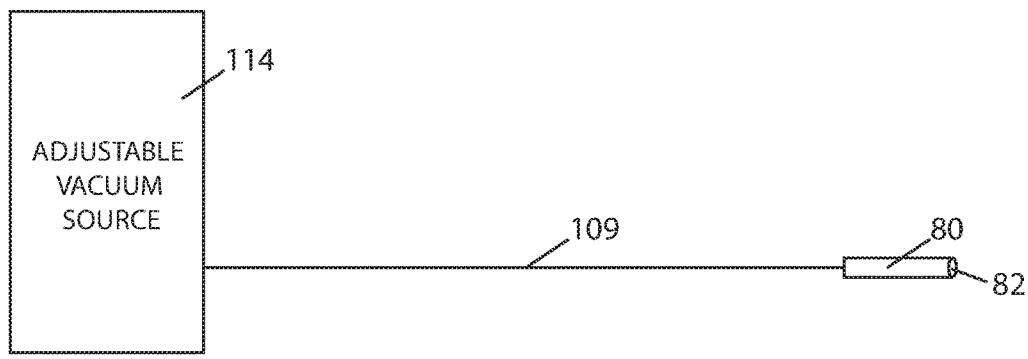
FIG. 1A is a schematic illustration of a surgical aspiration system of the prior art.

Number Legend 60 cyclic aperture flow regulator system
62 cyclic aperture flow regulator actuator portion
64 cyclic aperture flow regulator valve portion
68 tissue disruption actuator
70 surgical handpiece
80 surgical probe
82 aspiration port
84 probe shaft
86 probe hub
88 surgical probe attaching thread
90 irrigation valve
92 irrigation valve signal cable
100 fluid source
102 irrigation line
104 irrigation probe
106 irrigation pressure sensor
108 irrigation sensor cable
109 direct fluid path
110 first fluid path
111 aspiration tube
114 adjustable vacuum source
116 fluid waste deposit
118 vacuum control valve
120 venting valve
130 Processor
132 cyclic aperture flow regulator controller
134 tissue disrupter driver
140 aspiration pressure sensor
142 actuator cable
143 flow regulator control cable
144 motion sensors cable
146 tissue disrupter driver cable
150 lensectomy console
160 oscillatorty actuator
162 flow regulator oscillatory shaft
163 seal
164 oscillatory blade
166 valve portion body
170 valve input
172 fluid passage
174 second fluid passage
178 valve slit
180 valve output
200 aperture with adjustable cross-sectional area
204 tissue fragment
206 passing tissue fragment
208 retained tissue fragment
240 fixed aperture RMS handpiece
242 handpiece enclosure
247 male thread
248 female thread
249 actuator enclosure
258 screw
260 rotary motor
262 rotary motor shaft
264 rotary position sensor
270 linear actuator
272 linear actuator shaft
274 axial position sensor
276 coaxial rotary joint
280 flow regulator rotary shaft
282 bearing
284 bearing
290 valve rotor
292 valve chamber
294 rotor lid
295 edge
296 rotor window
400 prior art handpiece
402 handpiece housing
404 irrigation tube
406 aspiration line connector
500 surgical handpiece 502 handpiece enclosure
504 irrigation tube
506 aspiration tube
508 irrigation sleeve
510 ultrasonic lensectomy probe
512 ultrasonic actuator
514 ultrasonic motion converter
520 "In-Tube" valve portion
522 handpiece axial tube
523 circulation space
524 shaft seal
525 shaft seal cover
526 shaft seal body
527 O-ring
528 bypass channel
530 fluid return port
600 surgical handpiece
610 surgical probe with partial valve portion and two fluid passages
634 fluid passage
638 outflow channel
710 surgical probe with partial valve portion and one fluid passage
800 oscillatory driven cyclic flow regulator handpiece
820 oscillatory "in-tube" valve portion
822 oscillatory shaft
824 in-tube piston for "in-tube" valve embodiment
826 piston window
828 piston ring
840 in-probe piston for "in-probe" valve embodiment
910 surgical probe with complete valve portion and one fluid passage
922 shaft distal feature
924 surgical probe rotor
926 rotor shaft matching feature
928 rotor window
930 spring
932 rotor retaining stricture
950 Surgical probe with valve and tissue fragmentation feature
952 spur
954 valve rotor with internal tissue fragmentation feature
956 tissue fragmenting ribs in rotor
970 irrigation-aspiration handpiece with flow regulator system
972 aspiration probe
974 I/A handpiece distal enclosure
976 I/A handpiece proximal enclosure
978 aspiration port

DETAILED DESCRIPTION OF THE PREFERRED EMBODIMENTS

Show in FIG. 1A is a schematic illustration of a surgical aspiration system of the prior art showing a fluid path 109 directly connecting an aspiration opening 82 of a surgical probe 80 with an adjustable vacuum source 114. FIG. 1C shows a surgical handpiece of the prior art 400 with a housing 402, an irrigation tube 404, an irrigation sleeve 104, an aspiration line connector 406 and surgical probe 80 attached at the distal end of handpiece 400. It can be seen in FIG. 1D showing hidden aspects of handpiece 400 that fluid path 109 traverses in direct tubular manner from the aspiration opening of surgical probe 80 to the aspiration line connector 406 traversing electro-mechanic ultrasonic actuator 512 and ultrasonic motion shifter 514. In the prior art the fluid path connecting aspiration line connector 406 with vacuum source 140 is contained within a single and direct aspiration tubing.

Figure 1B:
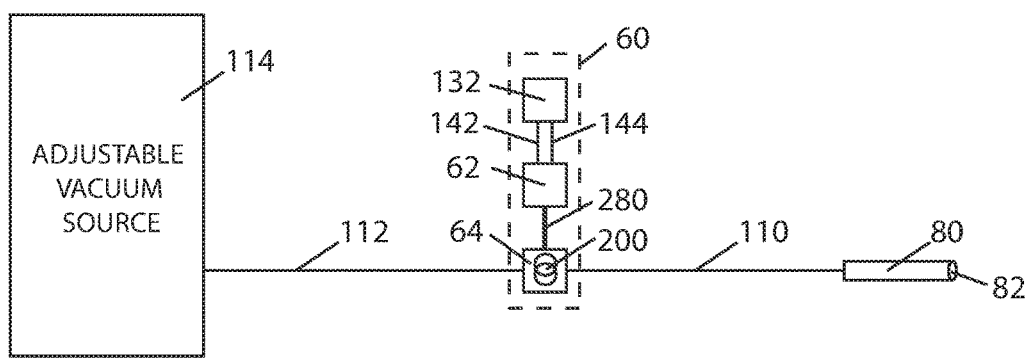
FIG. 1B is a schematic illustration of a surgical aspiration incorporating the cyclic aperture flow regulation system of the current invention.
Figure 1C:
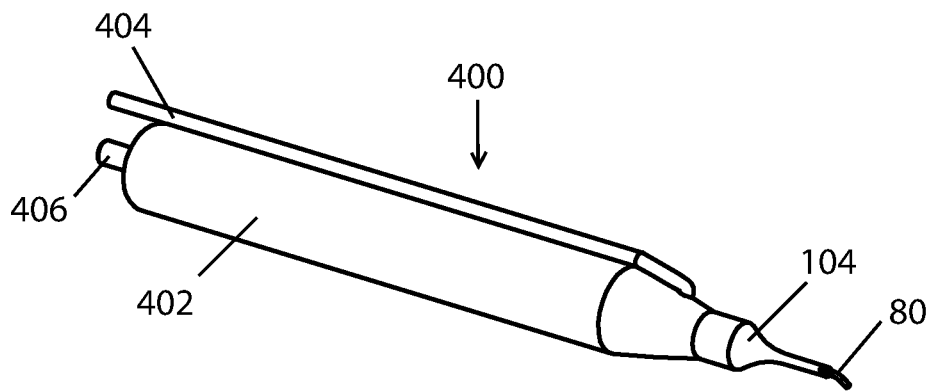
FIG. 1C is a perspective view of the exterior aspects of a surgical handpiece of the prior art.
Figure 1D:
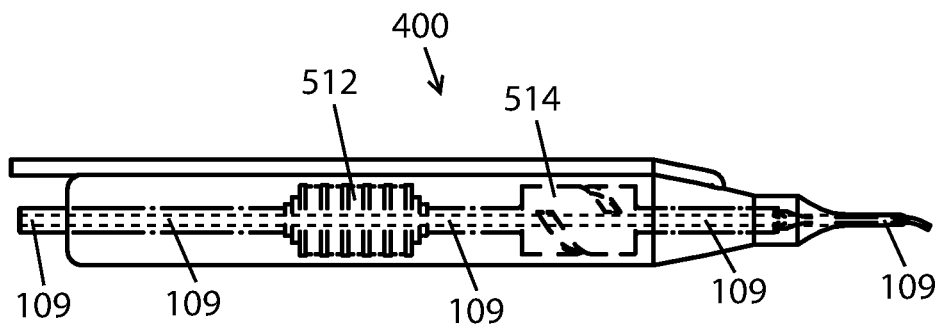
FIG. 1D is a side view of the handpiece from FIG. 1C exposing a continuous aspiration path.
Figure 1E:
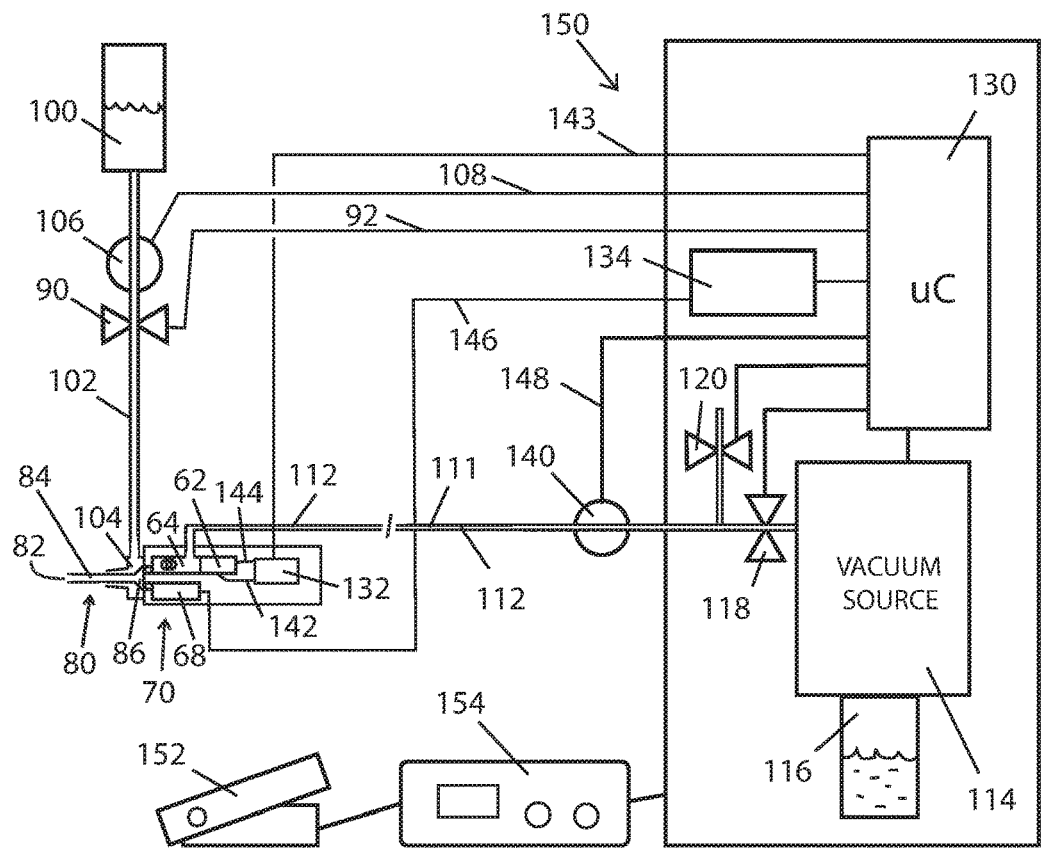
FIG. 1E is a schematic illustration of the cyclic aperture flow regulator system of the present invention incorporated into a phacoemulsification surgical console.
Figure 1F:
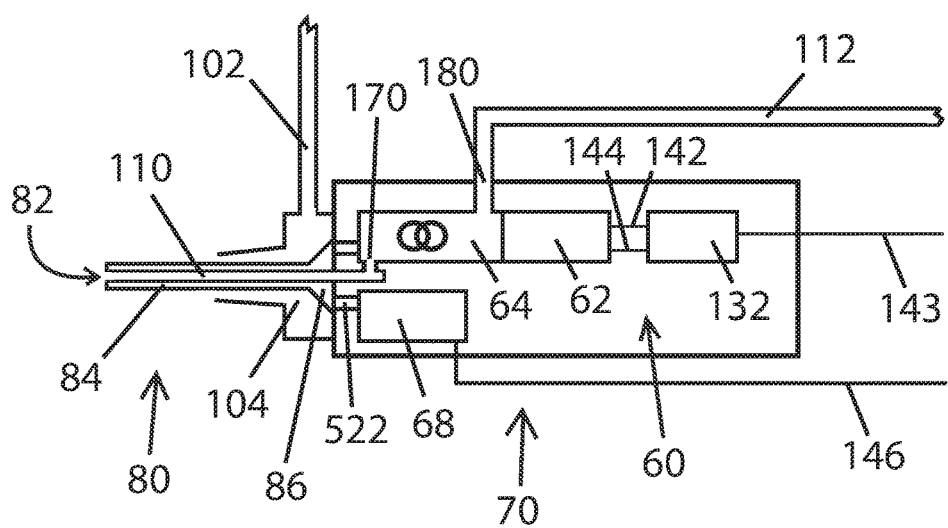
FIG. 1F is an expanded view of a handpiece portion from FIG. 1C.
Figure 2A:
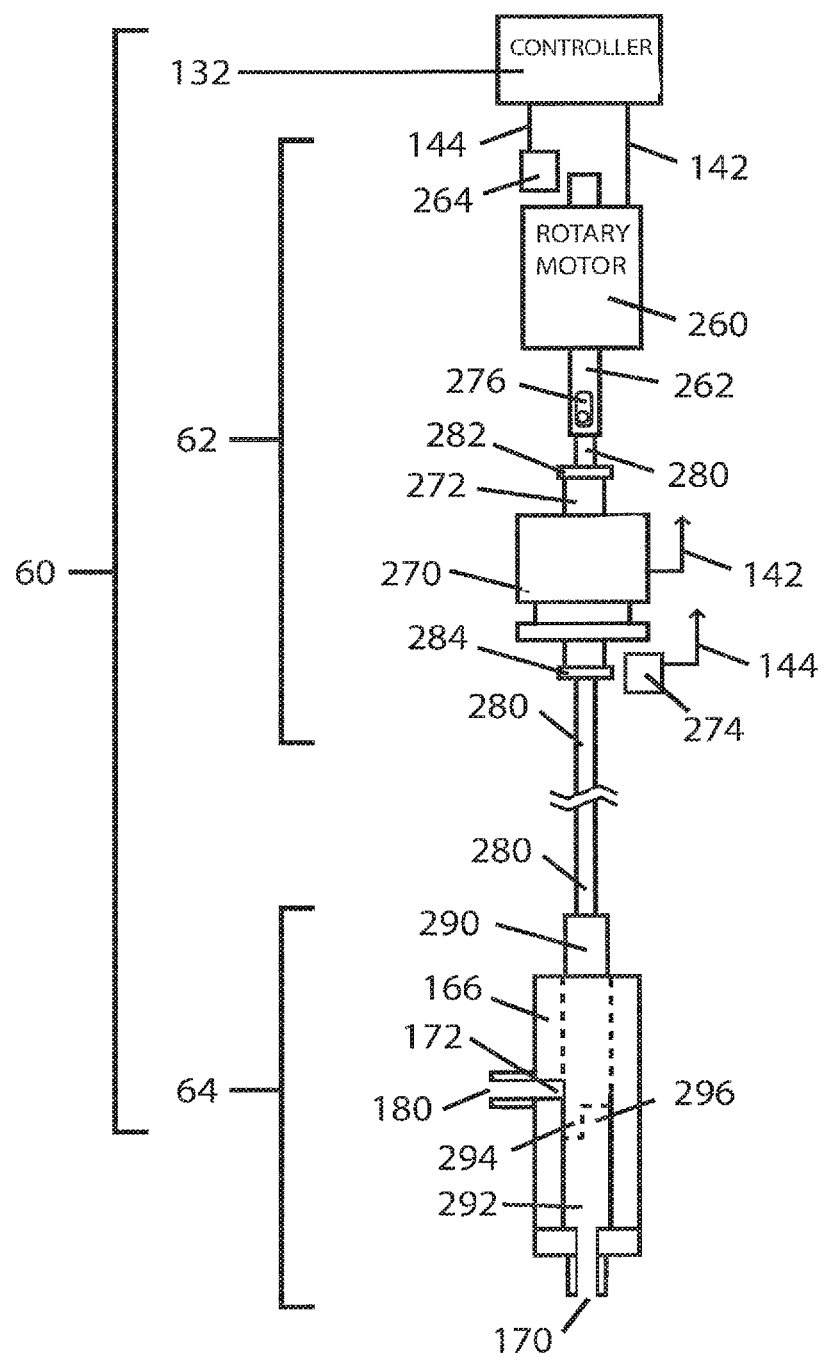
FIG. 2A is a schematic illustration one preferred rotary-axial embodiment of a flow regulator system of the present invention.

FIG. 1B is a schematic illustration of a surgical aspiration system incorporating a cyclic aperture flow regulator system 60 of the present invention. A valve portion 64 of system 60 is inserted in the fluid path between aspiration opening 82 and adjustable vacuum source 114. The fluid path is divided into a first (pre-regulator) fluid path 110 and a second (post-regulator) fluid path 112, both fluid paths fluidly connected through an aperture with adjustable cross-sectional area 200 inside valve 64. An actuator portion 62 of system 60 operates a shaft 280 to modify the cross-sectional area of aperture 200. A controller 132 provides cyclic commands through an actuator cable 142 to actuator portion 62 to cause cycles of variation of the cross-sectional area of fluid aperture 200. Controller 132 commands actuator portion 62 to substantially reduce the cross-sectional area of fluid aperture 200 during at least one portion of each cycle, the substantial reduction of the cross-sectional area including the option of a transient complete closure of aperture 200. Motion sensors in actuator portion 62 can provide motion feedback signals to controller 132 through a motion sensors cable 144

Shown in FIG. 1C is a schematic illustration of a cyclic aperture flow regulator system 60 of the present invention incorporated into a surgical handpiece 70 of a lens removing console 150. Shown in FIG. 1D is an enlarged schematic view of the handpiece 70 region from FIG. 1C and its components. An irrigation line 102 connects a source of pressurized fluid 100 to a surgical site through an irrigation probe 104. An irrigation valve 90 can regulate flow between fluid source 100 and probe 104 into the eye. Surgical probe 80 has an aspiration port 82 that can be inserted into a surgical site such as the anterior chamber of the eye. Aspiration port 82 is fluidly connected through a hollow probe shaft 84 and a probe hub 86 with an input 170 of a valve portion 64 of cyclic aperture flow regulator system 60 located surgical handpiece 70. Hub 86 also couples probe 80 with a tissue disruption actuator 68 inside handpiece 70 such that tissue disrupting energy can be effectively transmitted to probe 80 from tissue disrupter actuator 68 for lens disruption. First fluid path 110 is conformed between aspiration port 82 and aperture 200 including an input 170 of the valve portion 64 of flow regulator system 60. A reduced volume of first fluid path 110 is key for optimal performance of flow regulator system 60 when using high vacuum levels. Considering this observation, two preferred embodiments of flow regulator system have valve portion 64 of flow regulator system 60 located as near as practical to aspiration port 82 to reduce first fluid path 110 volume to a minimum.

First fluid path 110 is built with a cross-section preferably circular. Diameter should be equal or larger than the diameter of the fluid channel inside shaft 84 to prevent clogging this diameter typically ranging between 0.3 mm and 1.5 mm for a lensectomy probe. An output 180 of valve portion 64 of flow regulator system 60 is coupled to an aspiration tube 111 which travels a length to couple to vacuum source 114 within a surgical console 150. Second fluid path 112 is conformed between fluid aperture 200 and vacuum source 114 including output port 180 and aspiration tube 111. Vacuum source 114 has attached a fluid waste deposit 116.

A vacuum control valve 118 is inserted in second fluid path 112 to enable and disable vacuum available at output port 180. Valve 118 is commanded by processor 130. A venting valve 120 connects a lateral branch of second fluid path to an ambient or super-ambient pressure. Venting valve 120 can be activated by processor 130 to cancel vacuum inside second fluid path 112 and also to allow reflux operations requested by an operator. An irrigation line pressure sensor 106 can be installed in irrigation line 102. An aspiration line pressure sensor 140 can be installed in aspiration line 111. Cyclic aperture flow regulator system controller 132 can receive commands from processor 130 through a flow regulator control cable 143. An irrigation line pressure sensor signal cable 108 connects sensor 106 with controller 130. An irrigation valve signal cable 92 connects controller 130 with valve 90. Controller 130 operates a tissue disrupter actuator driver 134. Tissue disrupter driver 134 provides driving signals to tissue disrupter actuator 68 through a cable 146. Aspiration line pressure sensor 140 provides a pressure signal to controller 130 through a cable 148.

Handpiece with Axially Adjustable Rotor and "In-Tube" Valve Portion

FIGS. 2 to 8 illustrate different aspects of a preferred embodiment of the present invention. As seen in FIG. 2A, the cyclic aperture flow regulator system 60 of the present invention is composed by actuator portion 62 and by valve portion 64 with a valve portion body 166. A flow regulator shaft 280 transmits mechanical energy from actuator portion 62 to valve portion 64. Actuator portion 62 is composed by a having a rotary shaft 262 and by a linear actuator 270 having an axially displacing shaft 272. speed can be adjustable between 15 and 15.000 RPM. Linear actuator 270 has a loaded response time of 50 milliseconds when driven using a properly tuned PID controller. Shaft 280 receives rotary motion from rotary motor shaft 262 through a coaxial rotary joint 276. Shaft 280 also receives axial motion from linear actuator 270 through actuator shaft 272. Bearings 282 and 284 allow shaft 280 to freely rotate inside linear actuator shaft 272 while restricting any significant axial play between shafts 280 and 272. In this way, precise axial motion can be transferred to shaft 280 from linear actuator 270. A rotary position sensor 264 can detect motor shaft 262 angular position and provide an angular position signal to controller 132 through a cable 144. An axial position sensor 274 can detect flow regulator shaft 280 axial position and provide a shaft axial position signal to controller 130 through cable 144. Shaft 280 mechanically connects actuator portion 62 with valve portion 64. A valve rotor 290 is housed within a valve chamber 292 inside valve body 166 of valve portion 64 both rotor 290 and chamber 292 built with precise matching dimensions to allow axial and rotary displacement of rotor 290 inside chamber 292 without significant friction and at the same time with minimal leakage.

Valve chamber 292 is in fluid connection with valve input port 170. Valve chamber 292 is also in fluid connection with output port 180 through at least one fluid passage 172. Valve rotor 290 can have at least one lid 294 and at least one window 296 slidably in contact with the surface of chamber 292 where the entrance to passage 172 is located. Cross-sectional area of aperture 200 is configured by the overlay between lid 294 and window 296 both integral parts of rotor 290 and the entrance of passage 172. As shown in FIGS. 2B to 2D, depending on the relative axial and rotary position of rotor 290 with respect to body 166, lid 294 can partially or totally occlude fluid passage 172. Circular arrow "a" illustrates the rotary motion of shaft 280 and rotor 290. Linear arrow "b" illustrates the axial motion of shaft 280 and rotor 290. A fluid aperture 200 is determined by the relative position between lid 294 of rotor 290 and the entrance of fluid passage 172. Cross-sectional area of fluid aperture 200 is maximal when lid 294 does not overlap with any portion of the entrance of fluid passage 172. Cross-sectional area of fluid aperture 200 is minimal when a portion of lid 294 and/or of rotor 290 completely overlaps with the entrance of fluid passage 172 producing a substantial limitation to flow between ports 170 and 180 eventually determining a no-flow condition. A continuous range of intermediate aperture 200 dimensions are possible when partial occlusion of passage 172 occurs by different axial and rotary positions of rotor 290 with lid 294. In FIG. 2B valve rotor 290 is axially displaced into body 166 about ¾ of the full length that would otherwise totally cover fluid passage 172 in any rotary position. Three vertically disposed circles represent three different rotary positions of rotor 290 to exemplify three possible aperture 200 magnitudes along one revolution of rotor 290 in the depicted axial position.

In the top circle, rotor 290 and lid 294 in combination totally obliterate fluid passage 172 with aperture 200 being substantially closed or non-existent. The middle circle from FIG. 2B represents another rotational position of rotor 290 where lid 294 is minimally present in a way that mostly window 296 overlaps with passage 172 determining a moderate cross-sectional area of aperture 200. The lower circle from FIG. 2B shows another exemplary rotational position of rotor 290 that determines a very small aperture 200. Window 296 is the complementary cylinder portion of lid 294 that allows flow into passage 172 contributing to conform aperture 200. In the vertically arranged circles from FIG. 2C are represented similar rotor 290 rotational positions to the counterparts from FIG. 2B in this case with an axial position of rotor 290 that determines a an occlusion of about half the area of passage 172 entrance in any rotary position of rotor 290, leaving the other half of passage 172 entrance to be clear from obstruction or partially or totally occluded by lid 294 depending on the rotary position of rotor 290. The maximum aperture dimensions achievable during one revolution of rotor 290 are larger in FIG. 2C than in FIG. 2B. FIG. 2D is similar to 2B and 2C only that rotor 290 is axially positioned in a way that the only portion of rotor 290 that can overlap with passage 172 entrance during one revolution is lid 294. With rotor 290 in this axial position aperture 200 can reach the maximum possible cross-sectional area during one revolution of rotor 290 equivalent to the full aperture area of fluid passage 172 entrance.

Figure 3A:
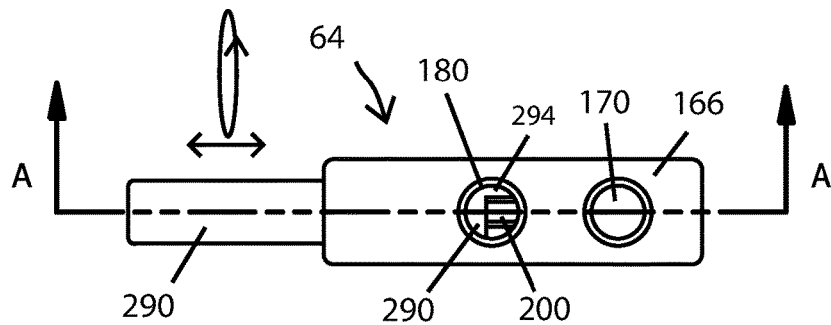
FIGS. 3A to 3D are sectional illustrations of a model of the flow regulator system from FIG. 2.
Figure 3B:
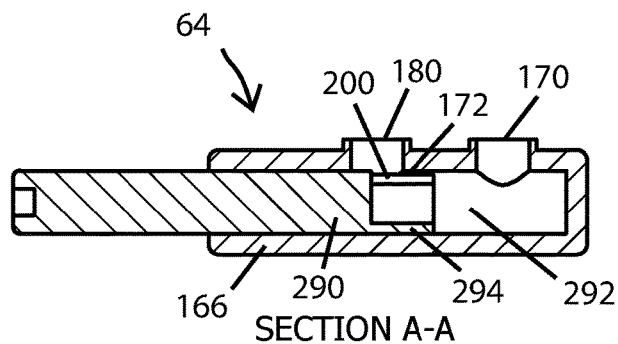
Figures 3C, 3D:
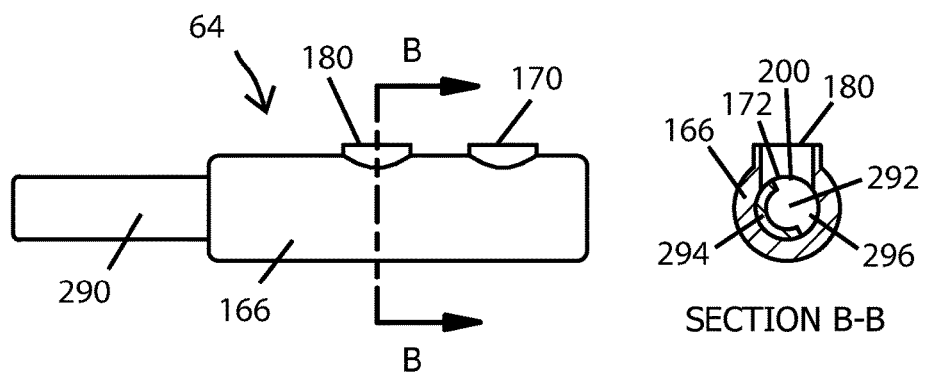
Figure 3E:
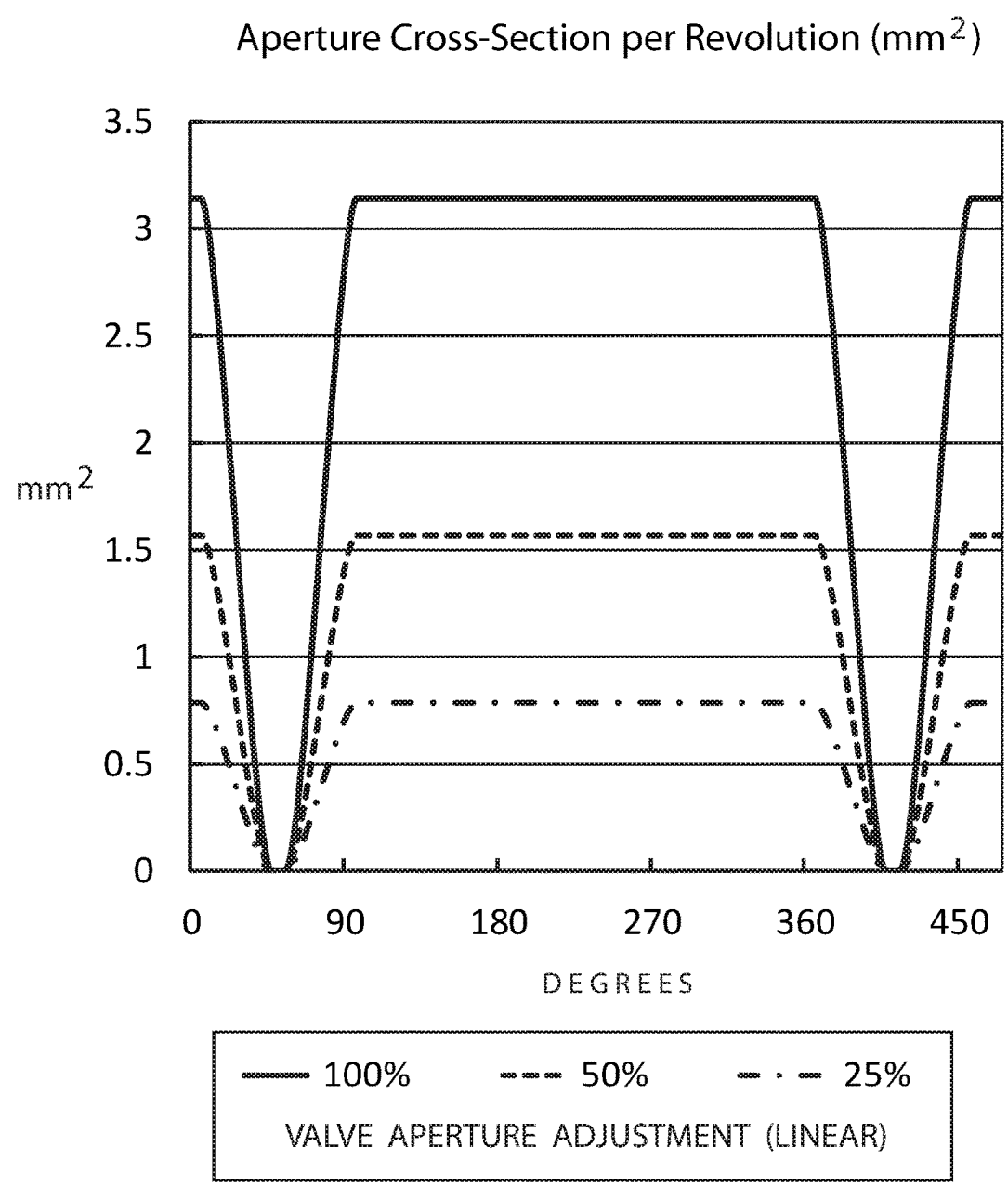
FIG. 3E is a graph illustrating the cross-sectional area of the adjustable fluid aperture along one revolving cycle of the flow regulator system matching with each of the examples shown in FIGS. 2B to 2D.

In FIGS. 3A to 3D are provided sectional views of valve portion 64 with rotor 290 in a particular axial rotary and axial position with respect to body 166 to illustrate how the magnitude of a fluid aperture 200 is determined by a combination of both the an axial and the rotary position of rotor 290. Although not necessarily planar, the narrowest aperture area is measured as the cross sectional area of aperture 200. FIG. 3E is a graph representing the aperture 200 dimensions versus rotor 290 rotary position while axially revolving rotor 290 inside valve chamber 292 along at least one revolution (degrees shown in X axis) in approximate correspondence with the examples provided in FIG. 2B (bottom tracing on the graph), FIG. 2C (middle tracing) and FIG. 2D (top tracing) for a circular fluid passage 172 entrance of radius=1 mm.

FIGS. 4A to 4K are representations of a surgical handpiece 500 for the removal of the crystalline lens from within an eye incorporating the cyclic aperture flow regulator system 60 of the present invention. Enclosure 502 accommodates and provides support for the interior components of handpiece 500. Irrigation line 102 is in fluid communication with an irrigation tube 504 which in turn connects with an irrigation probe 104 in the form of a coaxial irrigation sleeve 508. An aspiration tube 506 is in fluid communication with aspiration tube 111. An ultrasonically operated lensectomy probe 510 is fluidly and mechanically attached to handpiece 500 similar to probe 80 from FIG. 1.

Figure 4A:
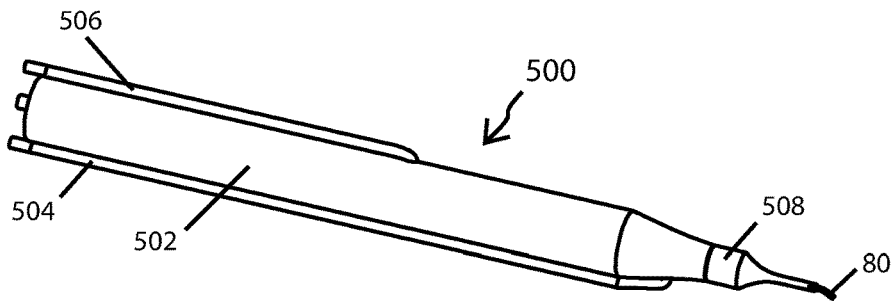
FIGS. 4A to 4K correspond to different perspective, detail and sectional views of one implementation in a surgical handpiece of the rotary-axial embodiment shown in FIG. 2A of the cyclic aperture flow regulator system.
Figure 4B:
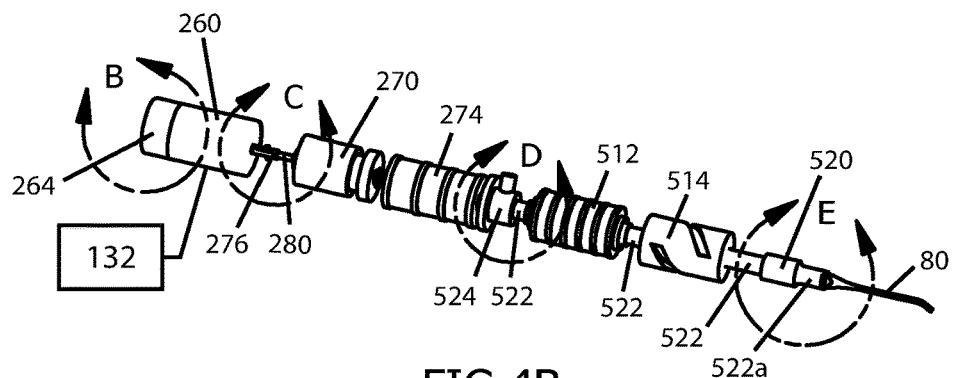
Figure 4C:
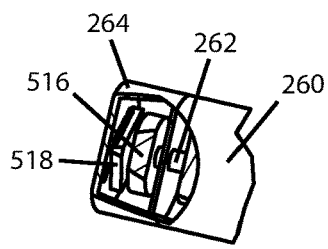
Figure 4D:
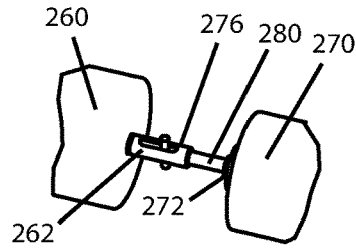

FIG. 4B shows the interior components of handpiece 500 as would be seen with enclosure 502 removed. An axial tube 522 has affixed an ultrasonic actuator 512 and an ultrasonic motion converter 514. A valve portion 520 is installed in tube 522 that corresponds with valve portion 64 from FIG. 1 conformed inside tube 522 ("In-Tube" configuration of valve 64). Lensectomy probe 510 is detachably connected both fluidly and mechanically with the distal end of tube 522 by means of a thread 88. The proximal end of tube 522 is connected with a shaft seal 524. Tube 522 interiorly contains axially disposed shaft 280 leaving a circulation space 523 between the outer diameter of shaft 280 and the inner diameter of tube 522 sufficient for expedite circulation of fluid and tissue fragments aspirated through probe 510. Shaft 280 crosses shaft seal 524 in watertight and gastight conditions to mechanically interconnect with rotary shaft 262 of rotary motor 260 though a coaxial rotary joint 276 (FIG. 4D). The opposite end of shaft 262 has attached rotary position sensor 264. Rotary position sensor 264 is composed by a radially magnetized circular magnet 516 fixated to the opposite end of motor shaft 262 and by a hall-effect rotary position sensor 518 (MELEXIS MLX90316 absolute rotary position sensor IC) (FIG. 4C).

Linear actuator 270 has shaft 272 coaxially mounted over shaft 280 providing shaft 280 freedom to rotate with respect to shaft 272 with no significant axial play as previously described. Linear motion sensor 274 consists in a linear variable differential transformer or LVDT (Measurement Specialties Series MHR+/−0.64 mm). Axial sensor 274 has a central hollow tube that is coaxially mounted around shaft 280 to allow non-contact axial and rotary displacements of shaft 280 with respect to sensor 274 while effectively measuring axial displacement of shaft 280. Among many alternatives for selecting axial sensor 274 are linear hall-effect sensors such as MELEXIS MLX90292 and linear optical quadrature encoders. Actuators 260 and 270 together with sensors 264 and 274 compose actuator portion 62 of cyclic aperture flow regulator system 60.

Figure 4E:
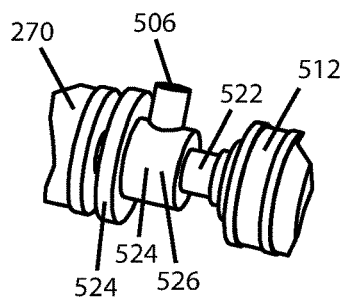
Figure 4F:
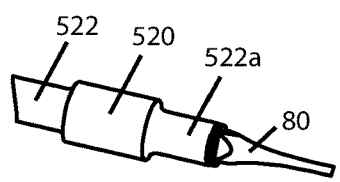
Figure 4G:
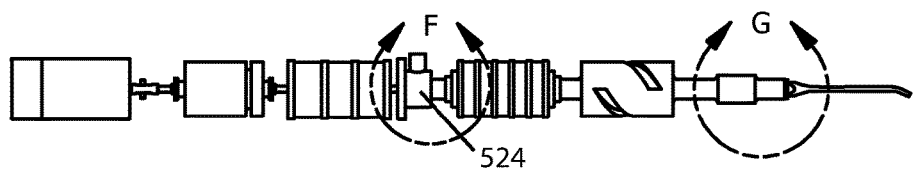
Figure 4H:
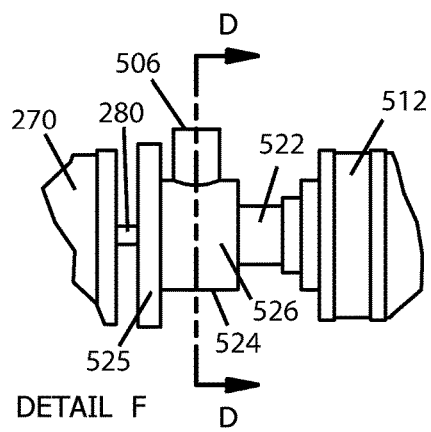
Figure 4I:
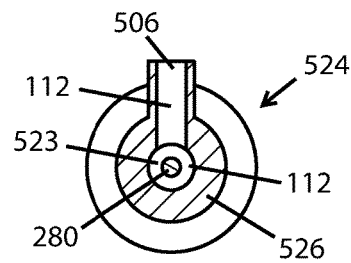

A detail of shaft seal 524 is shown in FIGS. 4E and 4H illustrating a shaft seal body 526 and a shaft seal cover 525 containing an O-ring 527 adjusted around shaft 280 (not shown). Shaft seal 524 allows low resistance watertight and airtight rotation and axial displacements of shaft 280 with respect to tube 522. Shaft seal 524 also contributes to fluidly connect the interior of tube 522 with aspiration tube 506 contributing to conform second fluid path 112 that fluidly communicates valve portion 520 with vacuum source 114.

Figure 4J:
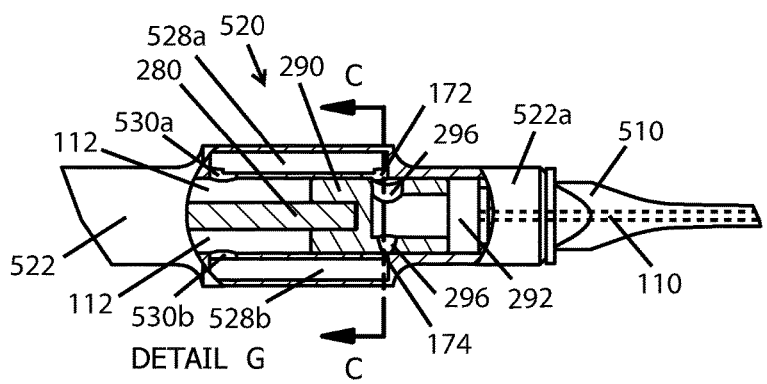
Figure 4K:
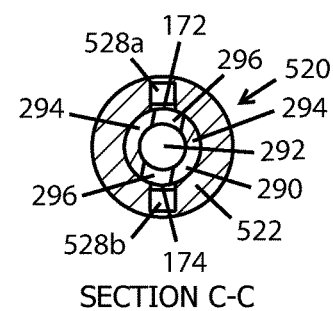

Detail G in FIG. 4G encircles "in-tube" valve portion 520 implemented inside tube 522 and is better illustrated in FIGS. 4J and 4K. FIG. 4J depicts a detail cutaway view of valve portion 520 integrated into a segment of tube 522. The portion of tube 522 that is left distal to valve 520 is labeled 522a and contributes to compose first fluid path 110. Cylindrical valve chamber 292 accommodates matching rotor 290 coupled to shaft 280 and enabled to rotate axially and to displace axially having two degrees of freedom (2 DOF) following shaft 280 rotary and axial movements as driven by actuators 260 and 270.

Probe 80 aspiration port 82 is in direct unobstructed fluid communication with valve chamber 292 through probe shaft 84, probe hub 86 and through distal portion 522a of tube 522 composing first fluid path 110. Fluid passage 172 and a symmetrically disposed second fluid passage 174 are in direct unobstructed fluid communication with the proximal interior of tube 522 across bypass channels 528a and 528b and through return ports 530a and 530b being all these fluid channels integral part of second fluid path 112. Channels 528 and return ports 530 can be functionally replaced by one or more channels etched on the inner wall of tube 522 using rotor 290 outer surface to complete the fluidic structure.

Aperture 200 defines the connecting boundary between first fluid path 110 and second fluid path 112. Valve chamber 292 can be fluidly connected with second fluid path 112 only when rotor 290 is disposed by shaft 280 in an axial and rotary position that allows a patent aperture 200 as illustrated in FIGS. 2 and 3. A variably sized fluid aperture 200 is determined by the extent of overlay between the entrance of fluid passages 172 and 174 and the fluid passage obstructing parts of rotor 290 including rotor body and lid 294. Non-blocking parts of rotor 290 are signaled as window 296. FIG. 4K is a cross sectional view extracted from FIG. 4J for better visualization of the rotational relationship between rotor 290 and chamber 292. It can be appreciated that during a single revolution of rotor 290 a fluidic aperture 200 can vary between maximum aperture and minimum aperture dimensions (cross-sectional area) producing a substantial variation in potential flow across the device. Aperture 200 dimensions can also vary between maximum aperture and minimum aperture with axial displacement of rotor 290. In this way a combination of axial and rotary displacements of rotor 290 can modify the cross-sectional area of fluidic aperture 200 between minimal and maximal. "In-Tube" valve portion 520 is illustrated in these figures as having a diameter larger than the diameter of tube 522 for better understanding. However, all the descripted fixed fluid channels from valve 520 can be carved or etched inside tube 522 without affecting its external diameter with similar performance. FIG. 8K is an expanded view of handpiece 500 to better illustrate the relationship between components inside valve portion 520, mainly shaft 280 and rotor 290.

The cyclic reduction of fluid aperture 200 cross-sectional area stops post-occlusion surges in a similar way an escapement mechanism in a clock avoids the escape wheel from accelerating progressively, also similar to engine braking that can stop a vehicle from running out of control. With valve 64 operating at low frequency, discrete "slices" of fluid are allowed to go through aperture 200 during each cycle. Increasing frequency of operation reduces the volume of these slices as well as the time separation between them. At a high enough frequency of operation of valve 64 aperture cycling the fluid "slices" merge into a continuum flow. When using high vacuum levels, cavitation inside first fluid path 110 together with fluid path resistance conform a fluidic RC circuit that operates as an integrator of the pressure and flow waves producing a steady level provided the frequency of the aperture reduction cycles is sufficiently high. This is one reason why increasing the frequency of the cycles substantially eliminates ripple from the pressure and flow waveforms. Fluid aperture cross-sectional area cycling that includes a substantial reduction of aperture dimensions during each cycle effectively limits maximum flow and prevents post-occlusion surges. The total volume of the summed cavitation bubbles inside first fluid path 110 is a determinant of the magnitude of post-occlusion surges. The smaller the volume of first fluid path 110, the smaller the magnitude of eventual post-occlusion surges in the system at maximum vacuum levels.

Particles contained in the fluid can be segmented by the cycling mechanism without impact on operation as shown in the sequence depicting snapshots during a single cycle of aperture 200 opening and closure from FIG. 16A to 16E.

Rotating rim 294 has an edge 295 that can be sharp to expedite tissue fragmentation. A tissue fragment 204 going with the flow across aperture 200 can be engaged by edge 205 in a way that fragment 204 is segmented. A portion 208 of tissue fragment 204 can be retained inside chamber 292 while another portion 206 of tissue fragment 204 can pass through aperture 200 into fluid passage 172. Repeated cycles of opening and closure of aperture 200 inside valve portion 64 at fast pace allow the clearance of all tissue fragments suspended in the fluid without compromise of the operation of the cyclic aperture flow regulator 60 of the present invention.

In operation the present invention is used with advantage to remove fluid and tissue fragments from a body cavity such as cataract fragments from within the anterior chamber of an eye. Surgical probe 80 is inserted inside the anterior chamber of the eye where the crystalline lens is to be removed. An operator first commands processor 130 from console 150 through user interface 154 and foot pedal 152 to open irrigation valve 90 to allow irrigation of fluid into the eye through irrigation probe 104. With irrigation enabled the operator can command to aspirate fluid and particles from inside the eye through distal opening 82 from surgical probe 80.

For operation of the flow regulator system of the present invention, the cyclic aperture modulation feature of flow regulator system 60 is enabled by powering rotary motor 260 to produce continuous rotation of rotor 290 inside valve 520 at a speed preferably above 2000 RPM in a way that rotation of rotor 290 produces at least one substantial reduction of the cross-sectional area of fluid passage 200 per rotor revolution, as determined by the axial position of rotor 290 inside chamber 292. With rotor 290 continuously rotating inside valve chamber 292 flow can be adjusted by commanding linear actuator 270 to axially displace the rotating rotor 290 inside valve chamber 292 into a position that will produce a desired flow rate according to a calibration protocol. There is an operating range regarding the axial position of rotor 290 inside chamber 292 where opening and also substantial closure of aperture 200 both exist within a single revolution of rotor 290. Excessive advancement of rotor 290 inside chamber 292 will produce permanent occlusion of aperture 200 regardless of the rotary position of rotor 290 by permanent overlay of the fluid passage 172 entrance with the body of rotating rotor 290, the valve remaining permanently in a substantially closed condition. Too little displacement of rotor 290 inside chamber 292 will determine too little exposure of lid 294 over fluid passage 172 entrance without significant reduction of aperture 200 dimensions during any portion of one revolution of rotor 290. In this condition transient substantial occlusions of aperture 200 will not occur during each cycle of revolution of rotor 290 the valve remaining in a permanently open position and losing the enhanced flow regulating attributes. A sub-ambient pressure or vacuum must be provided into second fluid path 112 by activation of vacuum source 114 and by the opening of vacuum control valve 118 while venting valve 120 remains in closed position.

It is relevant to describe two important relationships to better understand cyclic aperture flow regulator system operation:

a) Un-obstructed flow circulating into first fluid path 110 through probe port 82 and across valve 520 into second fluid path 112 for a given rotor 290 axial position is a function of the vacuum level inside second fluid path 110.

b) Un-obstructed flow circulating into first fluid path 110 through probe port 82 and across valve 520 into second fluid path 112 is a function of the axial position of rotor 290 inside chamber 292. For given form factors for rotor 290 and for valve chamber 292 including fluid passage entrance 172, different axial positions of rotor 290 determine different root mean square (RMS) computations of the cyclically varying dimensions (cross-sectional area) of aperture 200 along each revolution of rotor 290. Flow across valve 520 for a given vacuum level at second fluid path 110 is a function of the RMS aperture value.

In this way unobstructed flow rate across the cyclic aperture flow regulator system of the present invention can be adjusted in two main ways: 1) by determining the vacuum level inside second fluid path 112 and 2) by determining the axial position of rotor 290. A plurality of combinations of vacuum levels inside second fluid path 112 and rotor 290 axial positions can produce similar flow rates into unobstructed port 82. However the operator will notice differences in performance of surgical probe 510 when using low vacuum and high vacuum to obtain a similar aspiration flow rates. When using high vacuum tissue fragments will be aspirated forcefully even at low flow rate. When using low vacuum there will be less chance to damage surrounding tissues during complicated surgical maneuvers.

Flow rate can be adjusted by an operator by providing an input signal for example using foot pedal 152 to processor 130. Progressive foot pedal depression can instruct processor 130 to command linear actuator 270 to vary the axial position of rotor 290 to increase or decrease flow rate. Vacuum provided by vacuum source 114 into second fluid path 112 can also be varied by providing a command to processor 130. Both parameters, axial position of rotor 290 and vacuum level inside second fluid path 112 can be adjusted simultaneously to obtain a determined performance profile. The possibility of selecting a determined flow rate using different vacuum levels as enabled by the cyclic flow regulator system of the present invention is novel and valuable.

With irrigation enabled and aspiration enabled the operator can grasp tissue fragments and remove them from the eye by aspiration only eventually using the force of vacuum as the only lens disrupting energy. Alternatively, when cataract fragments are too hard for simple aspiration, a complementary source of lens disrupting energy such as ultrasound can be applied. Hub 86 couples surgical probe 80 with tissue disruption actuator 68 composed by an axial ultrasonic actuator 512 and an ultrasonic motion converter 514. In combination actuator 512 and converter 514 can transmit ultrasonic motion to surgical probe 80 providing an effective method to emulsify lens material. Depending on the driving frequency provided by tissue disruption driver 134 to actuator 68 the pattern of mechanical oscillation of probe 80 can be programmed to be parallel to the shaft axis (longitudinal) or alternatively, rotatory along the shaft axis (torsional). A noticeable feature of the cyclic aperture flow regulator system of the present invention is that motion of rotor 290 inside chamber 292 has rotary and axial component that are in coincidence with the eventual axis of displacement that can be transmitted to surgical probe 80 by tissue disruption actuator 68. This feature is of primordial importance because it allows simultaneous operation of the cyclic flow regulator system 60 and of tissue disruption actuator 68.

It is desirable to operate linear actuator 270 using a position feedback signal from linear displacement sensor 274. In this configuration actuator controller 132 receives shaft 280 axial position information and commands operation of linear actuator to locate rotor 290 at a desired axial set point to produce a desired unobstructed flow rate according to data from a calibration procedure stored in memory. The position feedback signal provided by sensor 274 allows to incorporate a control loop into actuator controller 132 using for example a proportional-integral-derivative filter (PID) to accurately and rapidly adjust the axial position of rotor 290 relative to valve chamber 292 according to the desired unobstructed flow rate set point commanded by an operator.

In a basic mode of operation of the cyclic flow regulator of the present invention flow rate for a given vacuum level is set by determining the axial position of rotor 290, while providing steady rotation to rotor 290 to produce cyclic fluctuation of aperture 200 cross-sectional area including at least one portion of substantial reduction of the cross-sectional area of aperture 200 during each cycle.

In some situations it can be of advantage to have control of the rotary position of rotor 290 for example when a determined axial alignment is desired between rotary lid 294 and fluid passage channels 172 and 174. This action can be of interest for example during a reflux operation or to ensure a permanently open aperture 200 if some malfunction is detected by controller 132 or processor 130. Rotary sensor 264 can provide a precise angular position signal to controller 132. Controller 132 can command rotary motor 260 to actively stop rotary shaft 262 at a selected angular position when using for example a brush-less DC motor that allows this operation.

A calibration routine can be performed at the beginning of each procedure during system priming. An example for a calibration routine can consist in: a) installation of a test chamber of the prior art to fluidly connect irrigation probe 104 with aspiration port 82, b) detection of a static irrigation pressure in the pressurized fluid source 100 using pressure sensor 106 with valve 90 closed, c) opening of valve 90 to allow flow from the pressurized fluid source 100 into fluid paths 110 and 112. d) provision of a determined vacuum level by activation of vacuum source 114, e) activation of rotary motor 260 to steadily rotate rotor 290 at the desired RPM, f) performing a data acquisition sequence along a series of step adjustments of the axial position of rotor 290 followed by storing in memory of the axial position of rotor 290, of the irrigation pressure reading from sensor 106 and of the vacuum reading from sensor 140 for each step, g) Calculation of the unobstructed flow rate for the measured steps of axial position of rotor 290 incorporating for this purpose irrigation line 102 resistance and the pressure drop measured between static pressure and steady state pressure, h) building of a transfer function to be used by controller 132 to adjust flow rate to a set point commanded by an operator by adjusting the axial position of rotating rotor 290 and the vacuum level from vacuum source 114. The calibration routine can also incorporate stepped measurements at different rotary motor speeds. Changing rotary speed of rotor 290 can result advantageous in some situation where for example, more ripple in the vacuum/flow wave within port 82 could help to attract or disrupt lens fragments. The calibration routine of flow regulator system 60 can also include determinations of flow rate with tissue disruption actuator 68 active at different power settings to adjust for flow drifts that can occur when both systems are operated simultaneously during surgery.

Reflux Operation: An operator can request a reflux operation by depressing a foot pedal switch when for example an unwanted portion of tissue is captured by distal opening 82 from probe 80. Reflux can be provided by providing a transient increase in pressure inside second fluid path 112 by transitorily closing valve 118 and opening valve 120 with valve 64 rotary motor 260 kept operating. The flow rate of the reflux operation (reflux speed) can be adjusted by simultaneously positioning rotor 290 in a desired axial position during the reflux. An alternative method for a reflux operation can consider stopping rotor 290 in such way that aperture 200 is kept continuously open during the duration of the reflux.

Operation of the cyclic aperture flow regulator system of the present invention provides several advantages over the prior art systems. Among the most relevant is that post-occlusion surge is virtually eliminated reducing the risk for complications. Maximally high vacuum levels can be used without post-occlusion surges increasing the efficiency to aspirate lens tissue fragments and reducing the need for complementary lens disrupting energies such as ultrasonic emulsification.

Another relevant advantage is the fact that this system operates in a way that unobstructed flow rate can be adjusted independently of the aspiration line vacuum level. This allows to set a low flow rate with a high vacuum for a slow but efficient removal of the crystalline lens material improving patient recovery time and operating room patient turnover.

Figure 15:
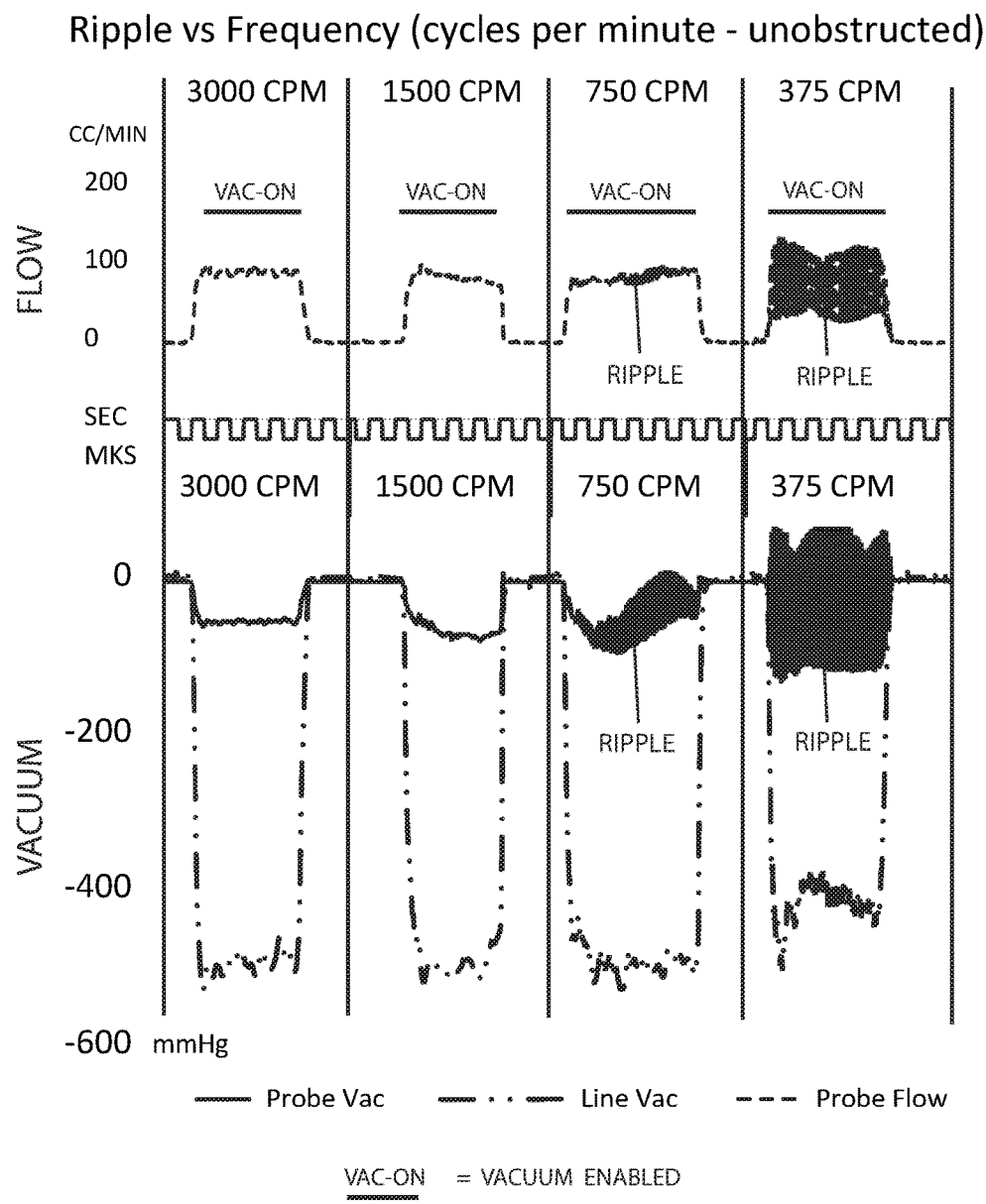
FIG. 15 is a graph depicting flow and pressure measurements at the aspiration opening of a surgical probe with a cyclic aperture flow regulator system of the present invention operating at different frequencies and illustrating that flow and pressure ripple diminishes above 750 CPM and transforms into a substantially steady flow at operation frequencies above 1500 cycles per minute.

Different combinations of aspiration line vacuum settings and unobstructed flow rate settings can be programmed and adjusted using the user interface 154 panels or foot pedal 152. These adjustments can be set fixed at the user interface or can vary continuously responding for example to levels of foot pedal depression. As can be seen in the graph in FIG. 15, the pressure and flow ripple effects detected at aspiration port 82 produced by the cyclic aperture flow regulator system of the present invention is progressively reduced by increasing the frequency of the cycles of aperture cross-sectional area fluctuation to an extent where in becomes insignificant (above 2000 cycles per minute in this example).

Valve 520 can be located in a more proximal position of tube 522 as long as the volume of first fluid path 110 is kept low by design. Also a more proximal location of valve can be considered in application with less demanding specifications or when planning to use relatively low vacuum levels. An illustration of a more proximal location of valve 520 is provided in FIG. 8L.

Safety Considerations: During operation the cyclic aperture flow regulator system 60 of the present invention produces intermittent substantial reductions of the dimensions of a fluid aperture 200 at high frequency. This mode of operation produces a substantially steady flow through surgical probe 80 into an aspiration line that can be adjustable between about no flow and a maximum flow. Safety measures must be implemented when operating flow regulator system 60 in combination with a tissue disrupter actuator that can generate heat such as with ultrasonic phacoemulsification. Low flow is a known risk factor for corneal burns (also known as incisional thermal injuries) produced by surgical probes during ultrasonic phacoemulsification. It is desirable that controller 132 from regulator 60 communicates with processor 130 from console 150 to avoid operational conditions that can be considered of risk of promoting a surgical complication such as a corneal burn. For example a minimum steady flow rate can be determined by regulator 60 aperture settings and by vacuum source 114 settings before activation of tissue disrupter actuator 68 if this operation involves potentially harmful heat generation. Also, a malfunction could occur that produced an unexpected continuous significant restriction to flow inside valve 64. This condition could occur for example if one actuator ceased to operate leaving rotor 290 permanently in a fluid passage blocking position. Controller 132 can detect such condition from the signals from sensors 264 and 274 and transmit a failure alarm signal to processor 130 or to an operator to take measures to take preventive measures to avoid a complication such as cutting ultrasound energy off. Failsafe actuators can also contribute to reduce the risk of permanent fluid passage blockage. For example, motor 260 can incorporate a centrifugal mechanism that produces axial retraction of shaft 262 when the rotary speed of the motor is below a safety limit. In this condition retraction of shaft 262 displaces rotor 290 through shaft 280 into a "safe mode" position inside chamber 292 in which no part of rotor 290 can block the entrance of fluid passages 174 or 174 the flow regulator valve remaining in an open status.

Handpiece with Axially Adjustable Rotor and "In-Probe" Valve Portion: Surgical Probe includes Part of Valve Portion 64.

Figure 5A:
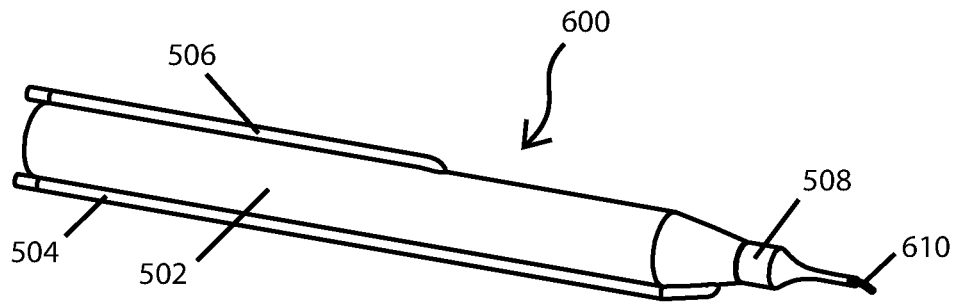
FIGS. 5A to 5C details the internal arrangement of parts in a surgical handpiece incorporating an additional rotary embodiment of the flow regulator system with the valve portion disposed inside a surgical probe.
Figure 5B:
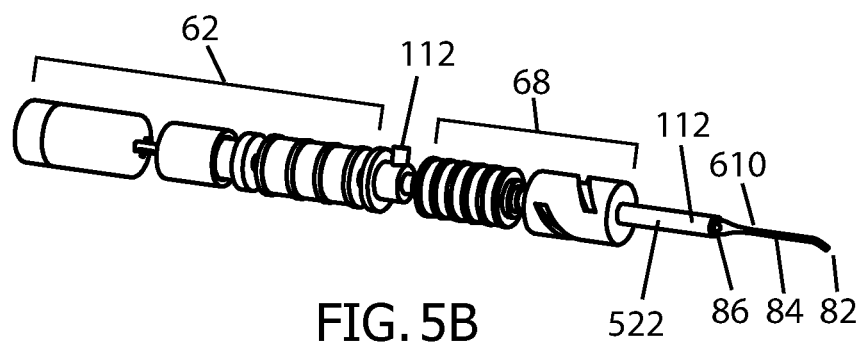
Figure 5C:
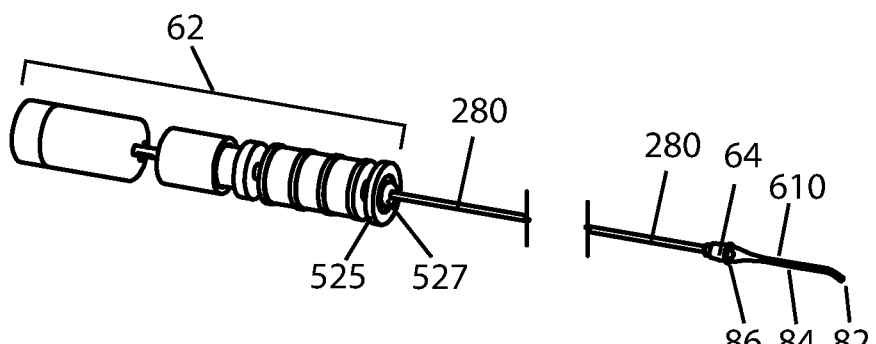
Figure 5D:
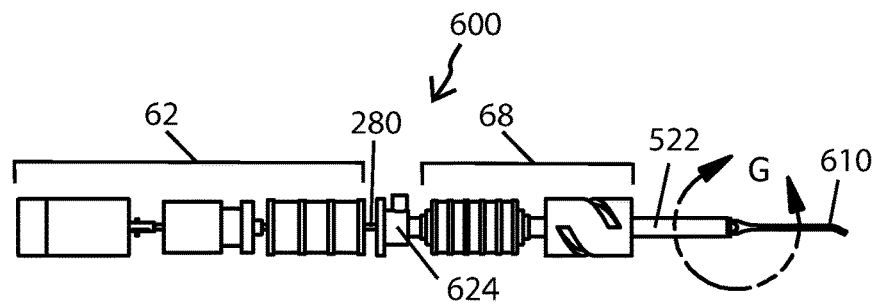
FIGS. 5D to 5G shows detail sectional views of the valve portion from FIG. 5A.
Figure 5E:
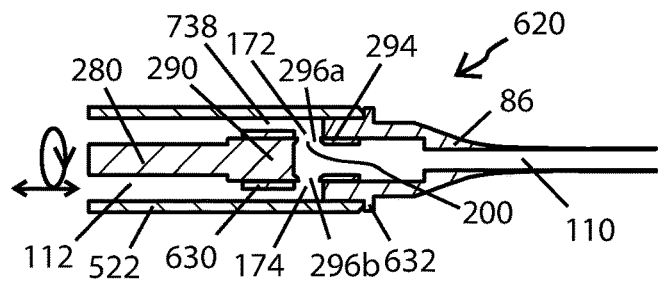
Figure 5F:
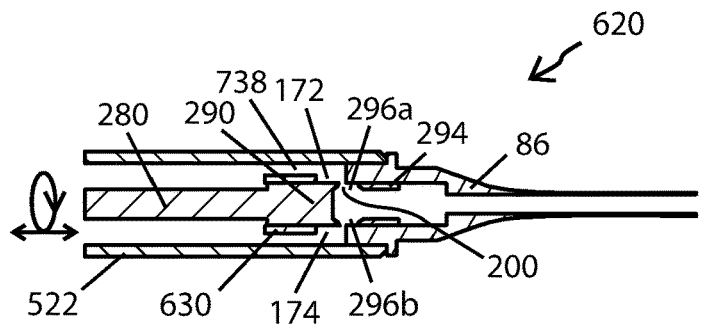
Figure 5G:
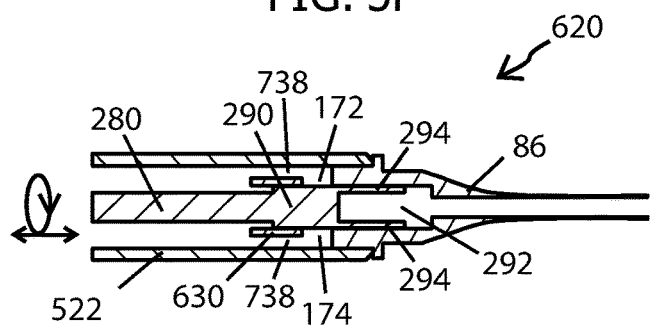
Figure 6A:
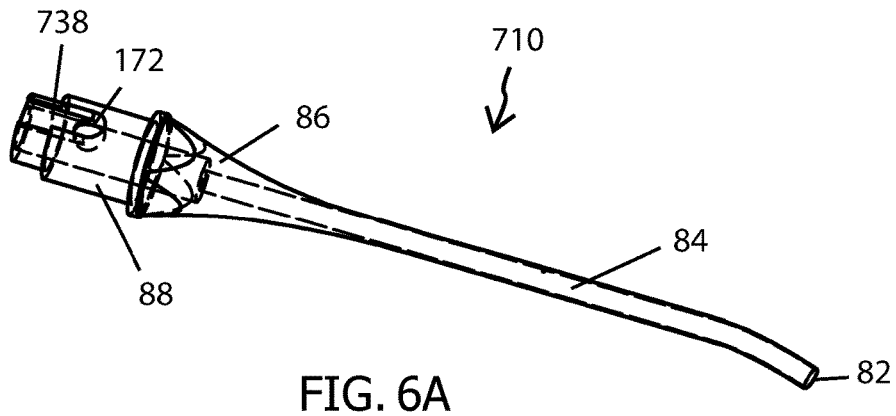
FIGS. 6A to 6C depict perspective and sectional views of a surgical probe that provides in part the composing elements of the valve portion of the flow regulator system of the present invention.
Figure 6B:
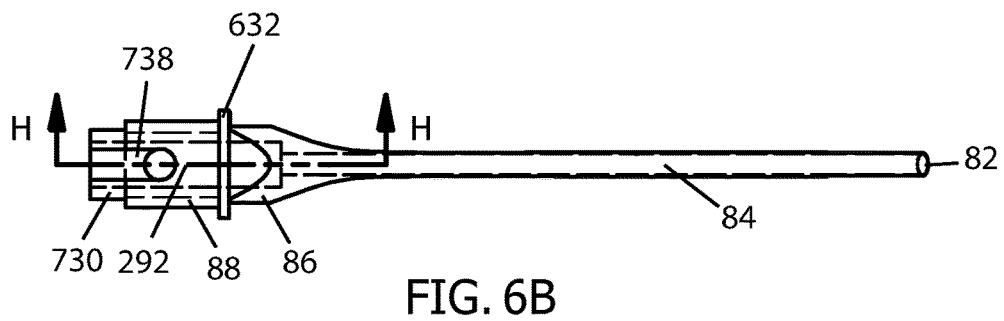
Figure 6C:
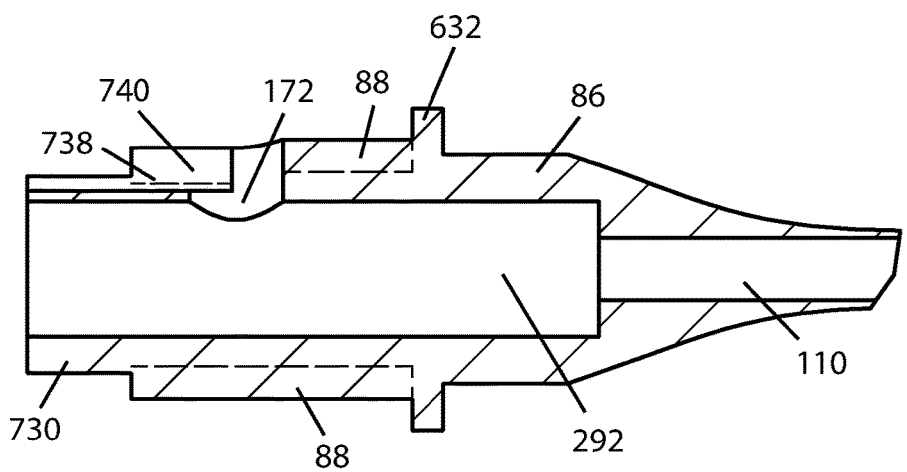
Figure 7A:
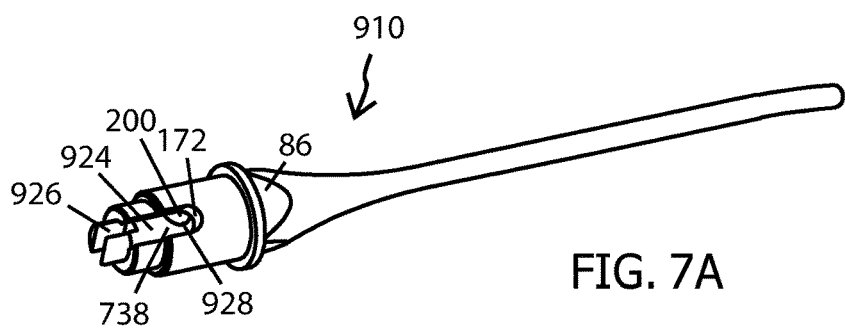
FIGS. 7A to 7E depict perspective and sectional views of a surgical probe that provides all the composing elements of the valve portion of the flow regulator system of the present invention.
Figure 7B:
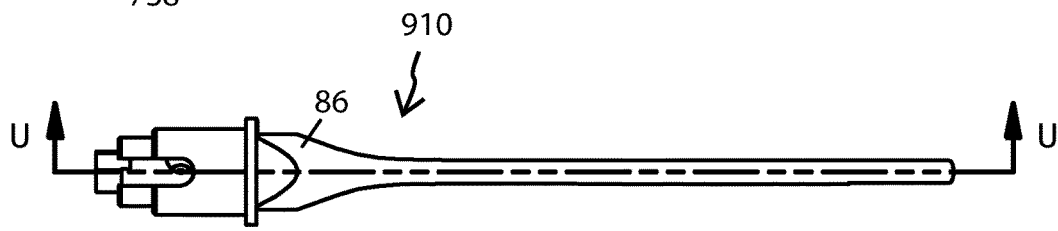
Figure 7C:
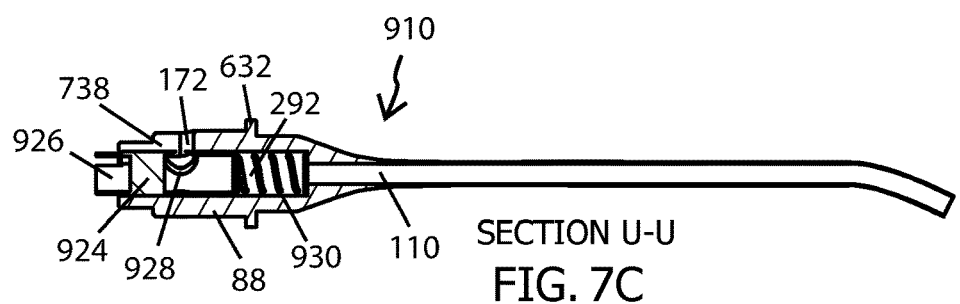
Figure 7D:
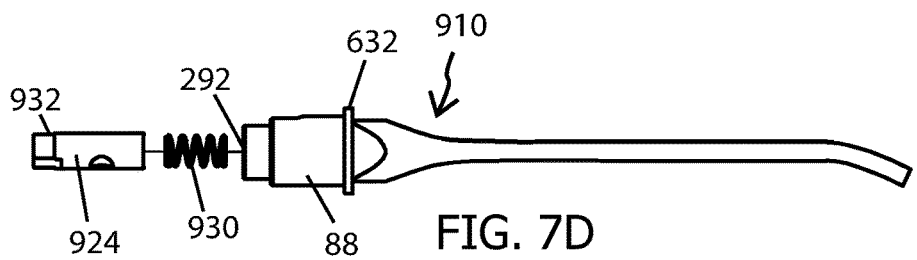
Figure 7E:
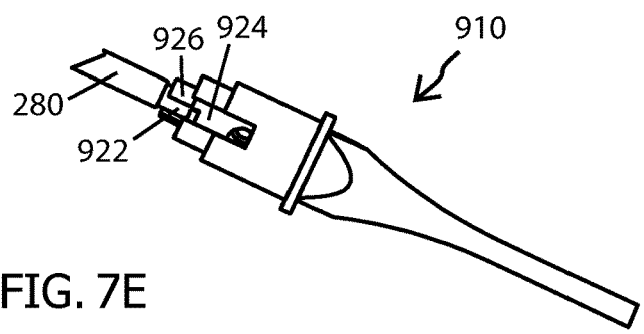

FIGS. 5A to 5G illustrate aspects of an additional embodiment with valve portion 64 of the cyclic aperture flow regulator system 60 of the present invention incorporated into a surgical probe 610 as an alternative approach to reduce the volume of first fluid path 110 to a minimum for use with maximum vacuum levels and still provide high flow stability. A handpiece 600 is shown in FIG. 5A with attached surgical probe 610. Handpiece 600 is shown in FIG. 5B with enclosure 502 removed showing actuator portion 62 of flow regulator system 60 disposed similarly as previously detailed in FIG. 4. In FIG. 5C is seen handpiece 600 with tissue disruption actuator portion 68 and with tube 522 both removed to expose underlying shaft 280 and surgical probe 610. In this embodiment shaft 280 is extended in a way that shaft 280 distal end is operatively in contact with the hub region 86 of surgical probe 610 which contains valve portion 64. FIG. 5D shows surgical probe 610 operationally coupled with tube 522. FIGS. 5E to 5G show slice views of detail region G from FIG. 5D. Rotor 290 is incorporated at the distal end of shaft 280 and with attachment of probe 610 to tube 522 becomes functionally disposed within valve chamber 292 enclosed by a chamber wall 630 to conform a complete valve portion 64. In this embodiment rotor 290 has a lid 294 of tubular shape with two circular openings that conform two windows 296a and 296b (also seen in FIG. 8F). Probe 610 incorporates to fluid passages 172 and 174. The extension of the overlay between the entrance of passages 172 and 174 with windows 296a and 296b in lid 294 determines the cross-sectional area of aperture 200. In FIG. 5E rotor 290 is shown positioned in such axial and rotary manner that windows 296a and 296b substantially coincide with the entrance of fluid passage channels 172 and 174 determining an aperture 200 of near maximum dimensions. In FIG. 5F rotor 290 is shown positioned in such axial and rotary manner that windows 296a and 296b partially coincide with the entrance of fluid passage channels 172 and 174 determining an aperture 200 of intermediate dimensions. In FIG. 5F rotor 290 is shown positioned in such axial and rotary manner that windows 296a and 296b do not coincide with the entrance of fluid passage channels 172 and 174 determining a substantial reduction of aperture 200. FIGS. 6A to 6C illustrates with further detail perspective, top and sectional views of a surgical probe 710 incorporating a valve portion 64 including chamber 292 with a single fluid passage 172. Surgical probe 710 provides the fixed constituent parts of valve portion 64 within hub region 86. These parts are essentially valve chamber 292 confined by a chamber wall 730 with one fluid passage 172. As seen in FIG. 6C a valve discharge channel 738 is usually conformed by a cutout volume 740 from hub 86 in combination with the internal wall of tube 522 (FIG. 5E). Valve discharge channel 738 fluidly connects fluid passage 172 with circulation space 523 inside tube 522 all being contributing parts to second fluid channel 112. A hub rim 632 is disposed to provide a hermetical seal between tube 522 distal end and hub 86 during operation both compressed by the tight fit of thread 88. Rotor 290 is an integral part of handpiece 600 and is functionally disposed inside chamber 292 when probe 710 is operationally attached to handpiece 600. This embodiment allows to frequently replace the fixed portion of valve 64 by replacing surgical probe 710 before degradation of system 60 performance by wear of valve chamber 292 of valve portion 64. Rotor 290 can be manufactured of materials resistant to wear such as ceramics, stainless steel or titanium in a way that it can resist wear over more extended use. FIG. 8M is an expanded view of handpiece 600 and surgical probe 610 to better illustrate the complementary action of parts from: 1) handpiece 600 at least providing actuator portion 62, shaft 280 and rotor 290, and 2) surgical probe 610 providing valve chamber 292 of valve portion 64 all parts cooperating to conform the cyclic aperture flow regulator system 60 of the present invention.

Handpiece with Axially Adjustable Rotor and "in-Probe" Valve Portion: Surgical Probe Includes Complete Valve Portion 64.

Another additional embodiment is illustrated in FIGS. 7A to 7E where a flow regulating lensectomy probe 910 is provided with a complete valve portion 64 including a matching rotor 924 with rotor windows 928. Rotor 924 is supplied already inserted inside chamber 292. Rotor 924 has a circular stricture 932 that operates as a rotor retainer in combination with a lid provided by probe 910 to maintain the rotor in position. A spring 930 is axially disposed partially compressed inside valve chamber 292 to push rotor 924 toward the exterior end of the usable axial displacement range. Spring 930 can slide frictionless within chamber 292 and also with rotor 290 during rotation and compression. A shaft 280 incorporated into handpiece 600 has a distal end feature 922 designed to match a complementary feature 926 of rotor 924 producing a rotary interlock effective to coaxially transmit rotary motion to rotor 924 for valve operation. Shaft 280 can exert a controlled pushing action across rotor 924 against spring 930. In this way rotor 924 can be rotated and axially located with precision by the action of shaft 280 transmitting rotary and axial power as commanded by controller 132. Flow regulation operation is similar to the previously described embodiments. It can be advantageous to provide the cyclic flow regulator system of the present invention with this embodiment where the complete valve portion 64 of flow regulator system 60 is renovated with each probe 910 exchange avoiding degradation caused by repeated use.

"In-Probe" Valve Portion with Enhanced Tissue Fragmentation Feature

Figure 8A:
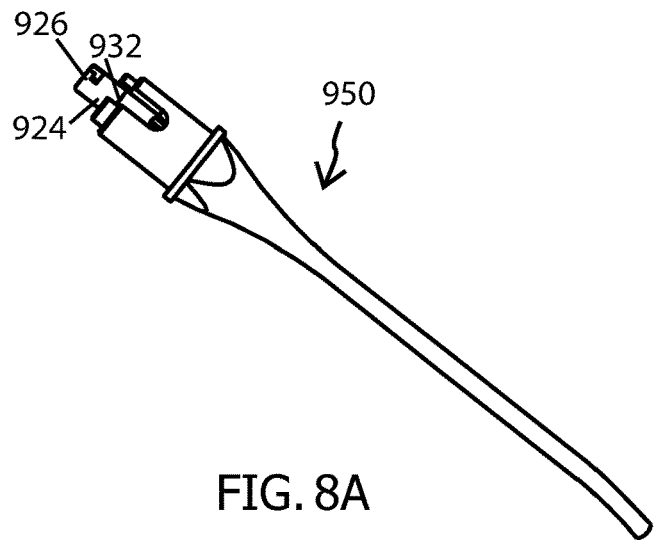
FIGS. 8A to 8J depict perspective and sectional views of another surgical probe that incorporates a complete valve portion of the flow regulator system of the present invention.
Figure 8B:
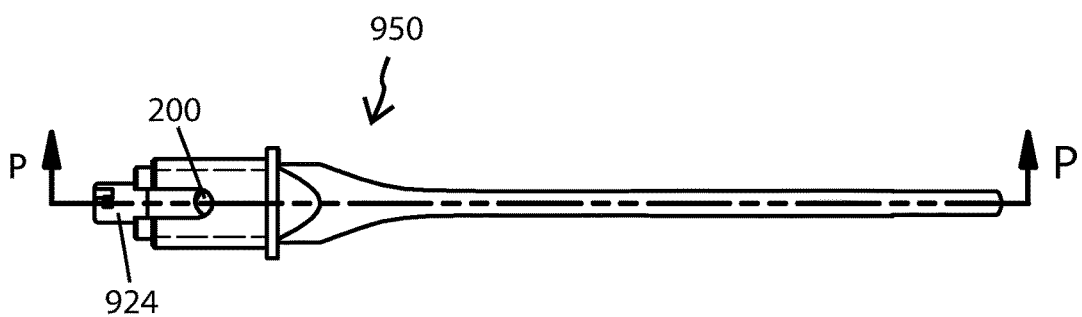
Figure 8C:
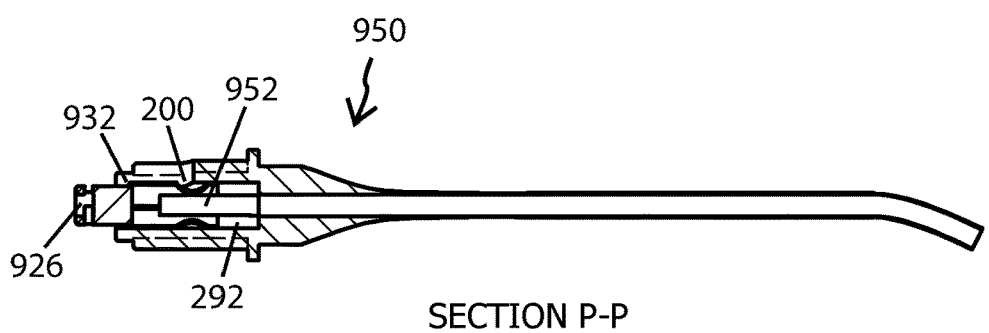
Figure 8D:
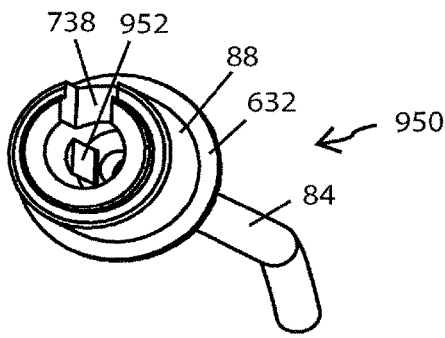
Figure 8E:
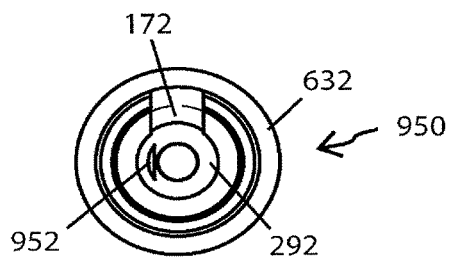
Figure 8F:
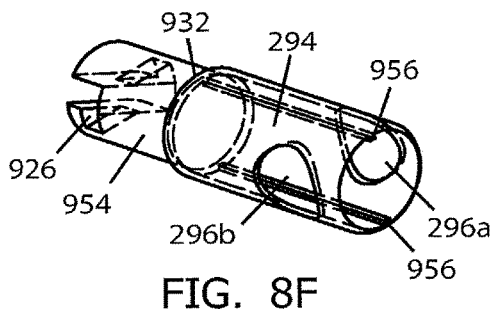
Figure 8G:
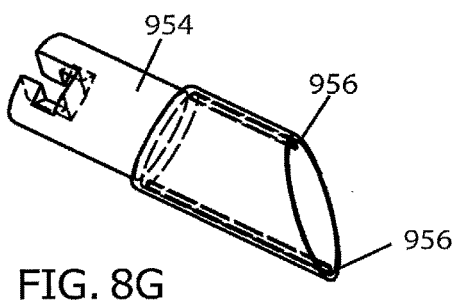
Figure 8H:
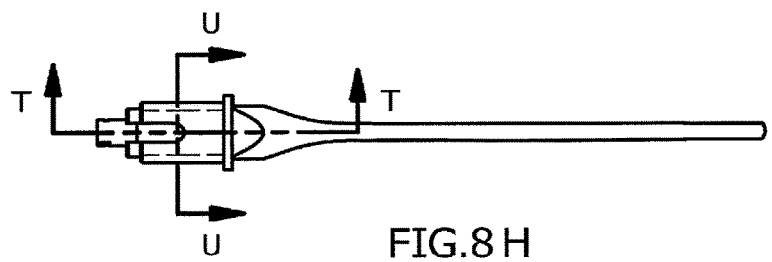
Figure 8I:
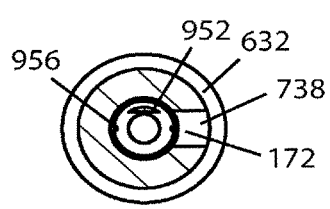
Figure 8J:
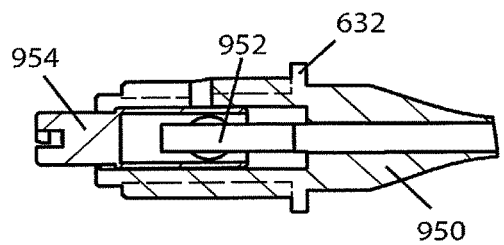
Figure 8K:
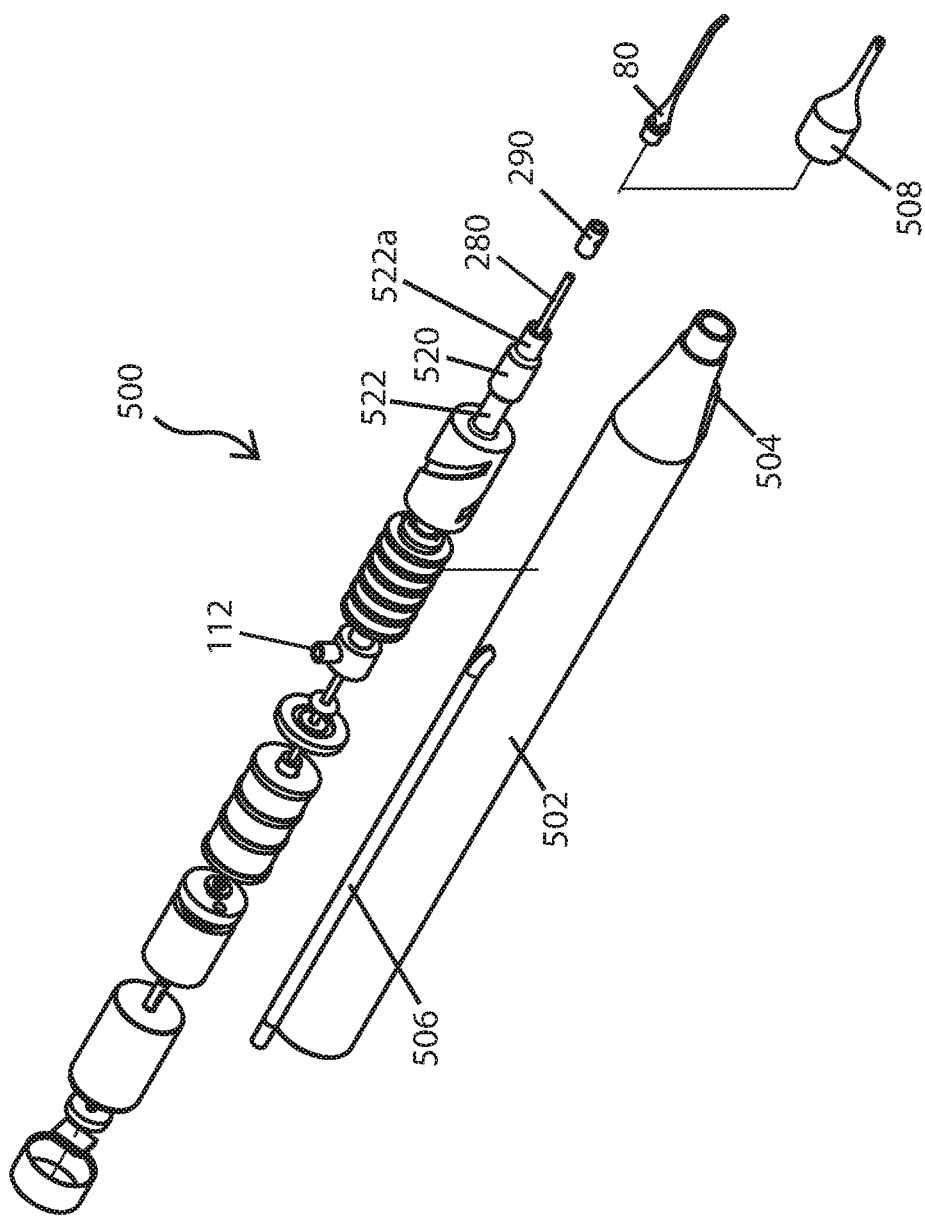
FIG. 8K is an expanded view of a surgical handpiece incorporating an "in-tube" valve portion of the flow regulator system of the present invention.
Figure 8L:
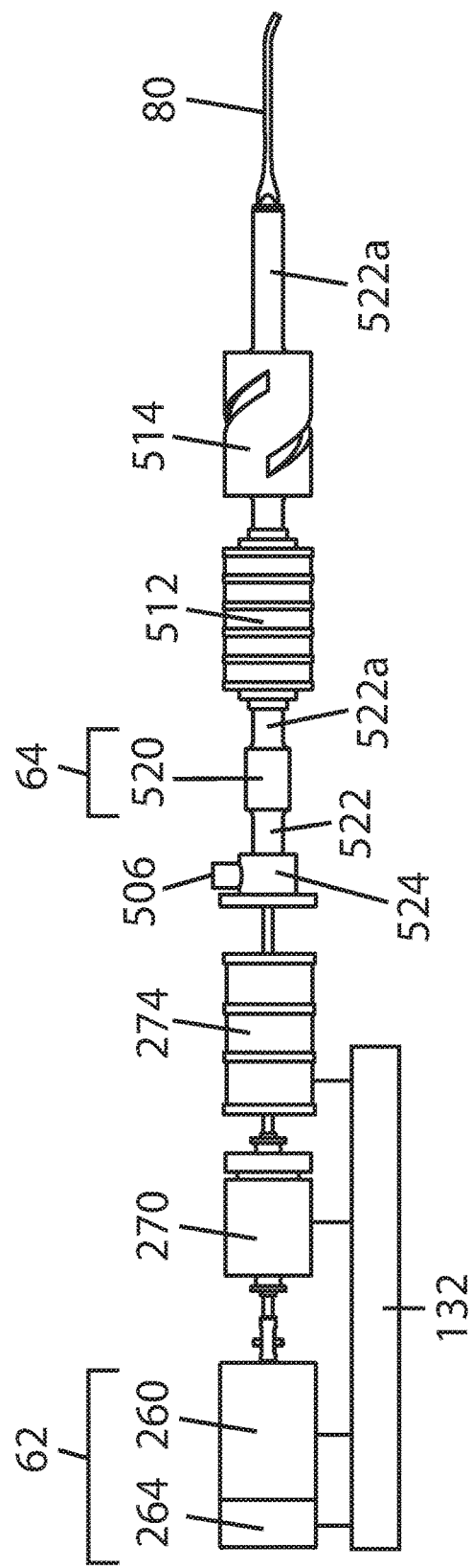
FIG. 8L is a side view of the interior components of a handpiece incorporating the valve portion of the present invention in a location more distant to the surgical probe than the tissue disrupting actuators.

A variant of the embodiment from FIG. 7 is illustrated in FIGS. 8A to 8J where a surgical probe 950 has a complete valve portion 64 further including an internal spur 952 integral with the bottom of valve chamber 292. A retained valve rotor 954 can additionally incorporate tissue fragmenting features such as sharp ribs operating in combination with spur 952 from probe 950 to compress and fragment tissue during rotation of rotor 954 inside chamber 292 attracted to the periphery by centrifugal force. A conventional rotor further incorporating sharp ribs 956 is shown in FIG. 8F. Incorporation of a spur inside valve chamber 292 leaves little space for spring 930. Therefore a more elaborate rotary-axial interlock between shaft 280 and rotor 954 is provided with this embodiment. This alternative interlock allows rotary and axial driving of rotor 954 by shaft 280 permitting an axial pulling and pushing action together with rotation without the need of a spring. Use of this embodiment with enhanced tissue fragmenting capabilities can enhance flow stability by further reducing the size of suspended tissue fragments enhancing valve operation and flow stability, particularly when fragments could be extremely hard.

Irrigation-Aspiration (I/A) Handpiece with Cyclic Aperture Flow Regulator System:

FIGS. 13A to 13D illustrate an embodiment of the present invention for use in an irrigation-aspiration surgical handpiece 970 equipped with a cyclic aperture flow regulator system of the present invention. A proximal enclosure 976 contains at least the rotary and linear actuators that conform the actuator portion 62 required for flow control operation and can also contain controller 132 (not shown). A smaller diameter distal enclosure 974 contains the distal portion of irrigation line 102 in fluid communication with irrigation probe 104. Enclosure 974 also contains axial tube 522 with an included "in-tube" flow regulator valve portion 520. An aspiration probe 972 having an aspiration port is coupled to the distal end of tube 522. First fluid path 110 is conformed between aspiration port of probe 972 and aperture 200 inside valve portion 520. This embodiment can be used with advantage to replace conventional irrigation/aspiration hand pieces with the advantage of enabling the use of very high vacuum with controlled flow. Handpiece 970 can allow to aspirate lens fragments through port of soft to medium density with a significant reduction in the use of additional lens disrupting energy. Similarly it can be used to remove more efficiently lens fragments from softened crystalline lenses for example after the use of a femtosecond LASER to soften the lens.

Figure 9A:
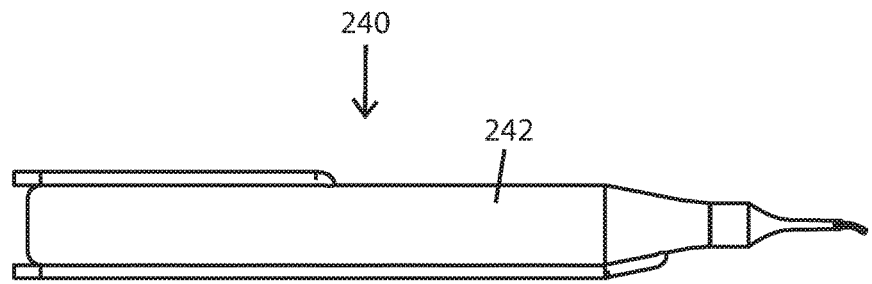
FIGS. 9A and 9B are side views of a handpiece incorporating an embodiment of the present invention with the adjustable fluid path operating with a fixed RMS value of the cross-sectional area.
Figure 9B:
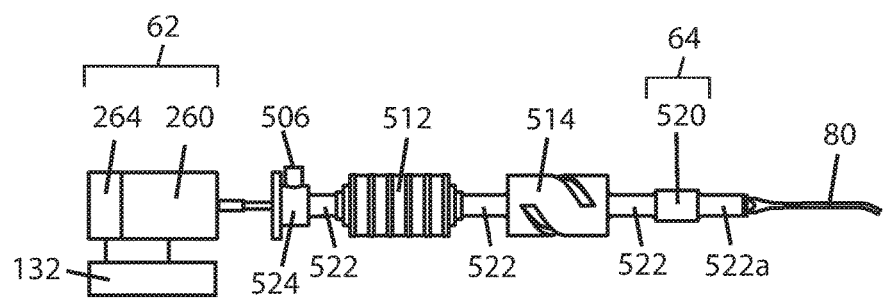

Handpiece having Flow Regulator System with Fixed Cross-Sectional Area RMS:

Illustrated in FIG. 9A is a side view of a surgical handpiece 240 having an enclosure 242. FIG. 9B depicts the interior parts of handpiece 240 with enclosure 242 removed. A rotary motor 260 is operable to rotate shaft 280 around its axis. This embodiment has no structure to support the adjustment of the axial position of shaft 280 and rotor 290 relative to chamber 292. During operation this embodiment produces rotation of rotor 290 inside chamber 292 in a fixed axial position producing cycles of variation of the cross-sectional area of aperture 200. During each rotary cycle of rotor 290 there is at least one portion of the cycle where the cross-sectional area of aperture 200 is substantially reduced or closed. In this embodiment the RMS value of the cross-sectional area of aperture 200 is fixed as provided and nonadjustable. When using this embodiment aspiration flow can be adjusted by varying the vacuum level provided by vacuum source 114.

Figure 9C:
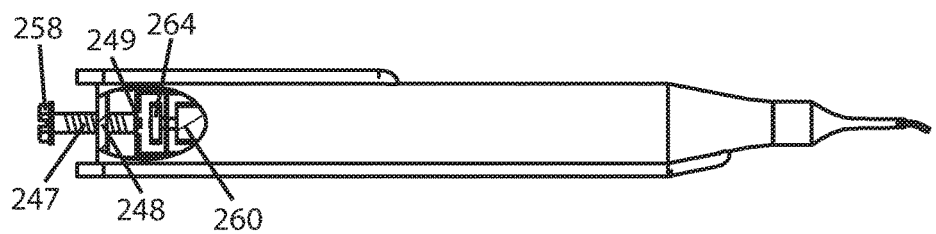
FIG. 9C is a side view of a handpiece similar to that shown in FIGS. 9A and 9B further incorporating a mechanism that allows an operator to manually adjust the RMS value of the cross-sectional area.

A variation of the embodiment shown in FIGS. 9A and 9B is shown in FIG. 9C where a screw 258 with a male thread 247 is provided passing through a female thread 248 in handpiece enclosure 242. Screw 258 is interiorly attached to an enclosure 249 of actuator portion 62 including sensor 264 and motor 260. Rotation of screw 258 produces an axial displacement of motor 260 and indirectly an axial displacement of shaft 280 and of rotor 290. An operator can manually adjust the axial position of rotor 290 inside chamber 292 by turning screw 258 and in this way modify the cross-sectional area RMS value of aperture 200. This action modifies the vacuum-flow relation of the flow regulator unit changing performance.

Figure 12:
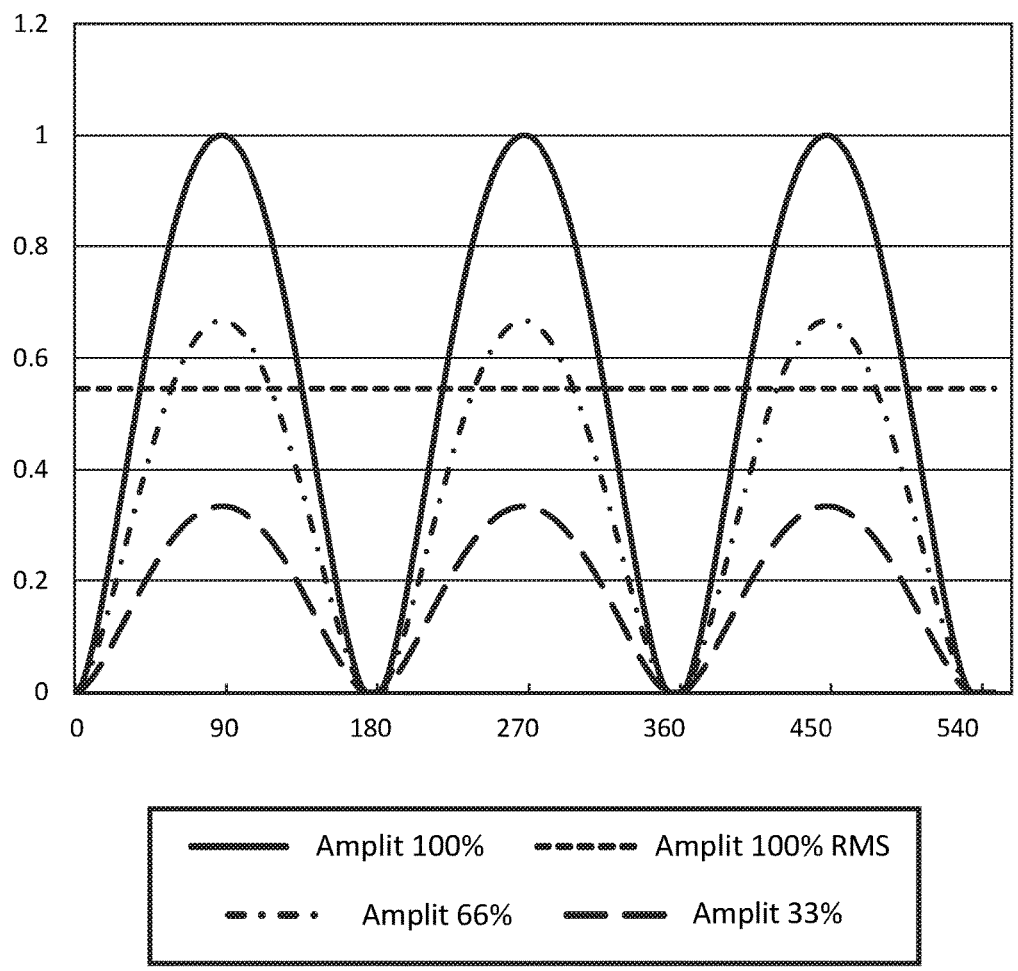
FIG. 12 is a graph illustrating the aperture cross-sectional area variation along one full cycle of oscillation from the examples from FIGS. 10A to 10J represented for three different linear oscillation amplitudes.

Cyclic Aperture Flow Regulator System Driven by Oscillatory Actuator:

FIG. 10A is a perspective view of a flow regulator system 60 having valve portion 64 and actuator portion interconnected by a shaft 162. In this embodiment valve portion 64 is mechanically actuated by a single oscillatory actuator 160 through shaft 162 that transmits vibratory motion. FIGS. 10C to 10D are cross sectional slice views from FIG. 10B. A valve body 166 has an input port 170 and an output port 180. Input port 170 and output port 180 are fluidly connected inside body 166 through two fluid passages 172 and 174. A slit 178 perpendicularly traverses both fluid passages. Slit 178 internally receives an oscillatory blade 164 having a window 176. Blade 164 is mechanically connected with shaft 162 to receive axial displacement from actuator 160. Shaft 162 has a watertight and airtight seal 163. Window 176 in blade 164 is positioned in a way that when actuator 160, shaft 162 and blade 164 are in a centered position, blade 164 totally obliterates both fluid passages 172 and 174 (FIG. 10C). Actuation of actuator 160 over shaft 162 to produce a proximal displacement of blade 164 locates window 176 over fluid passage 174 creating a first fluid aperture 200a (FIG. 10D). Actuation over shaft 162 by actuator 160 to produce a distal displacement of blade 164 locates window 176 over fluid passage 172 creating a second fluid aperture 200b (FIG. 10E). A "brake before make" concept can be considered in the design of valve 64 this meaning that a substantial reduction of the cross-sectional area of one fluid aperture must occur before the opposite fluid aperture begins to open. As illustrated in FIGS. 11A to 11J, blade 164 with window 176 oscillating around the centered position from FIG. 10C alternates between a first and a second fluid aperture 200a and 200b passing over the centered position two times during each cycle of oscillation. Operation of this embodiment occurs with actuator 160 energizing blade 164 to oscillate at a frequency fast enough to produce steady flow and minimal ripple, similar to the rotary embodiment. A typical frequency of oscillation would be above 50 hertz. In this embodiment flow rate can be adjusted by varying the amplitude of oscillations of blade 164 in a way that increasing the amplitude of oscillation will increase aperture dimensions subsequently increasing flow. Flow is a function of the RMS value of the sum of apertures 200 and 201 cross sectional-areas. As with the main embodiment, flow rate is also a function of the vacuum level at second fluid path 112. Thus a second modality to regulate unobstructed flow into a surgical probe is to increase vacuum to increase flow. The graph in FIG. 12 displays the total aperture (summed cross-sectional areas of apertures 200a+200b) along phase during 1.5 sine wave oscillations. The example corresponds to a prototype valve designed with equally sized circular openings for fluid passages 172, 174 and for window 176. Three tracings are provided. Top tracing corresponds to maximum oscillatory amplitude. Middle tracing corresponds to ⅔ of maximum amplitude and bottom tracing corresponds to ⅓ of maximum amplitude. The horizontal dotted line represents the RMS value for the cross-sectional area of the waveform in the top tracing.

Figure 13A:
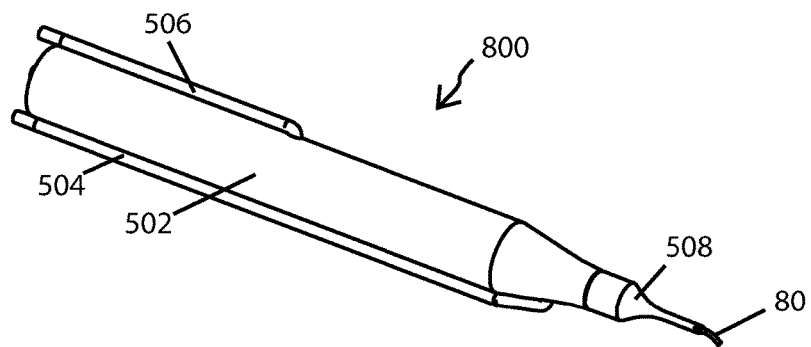
FIGS. 13A to 13H correspond to different perspective, detail and sectional views of one implementation in a surgical handpiece of the oscillatory embodiment shown in FIG. 10 of the cyclic aperture flow regulator system.
Figure 13B:
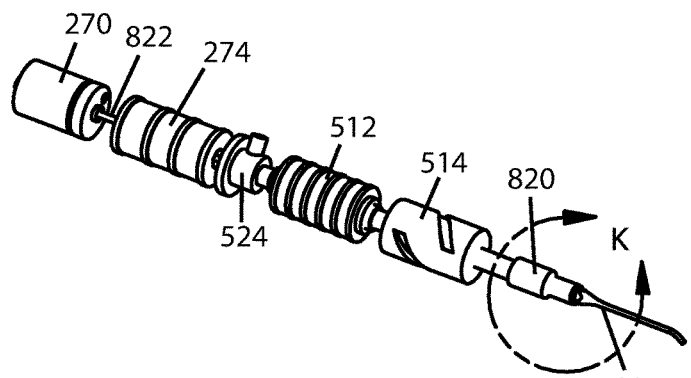
Figure 13C:
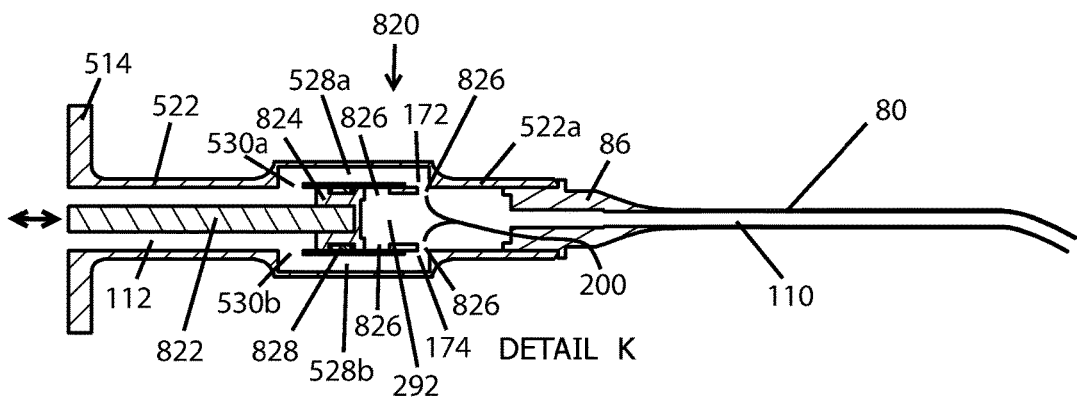
Figure 13D:
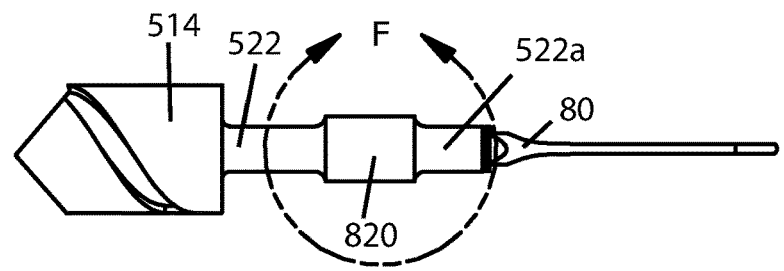
Figure 13E:
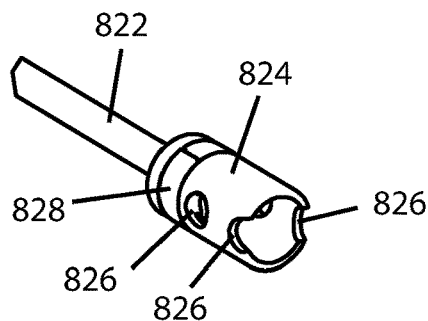
Figure 13F:
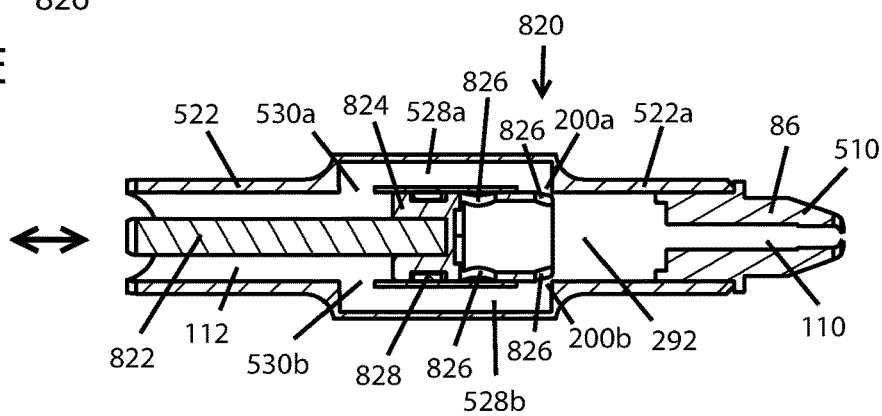
Figure 13G:
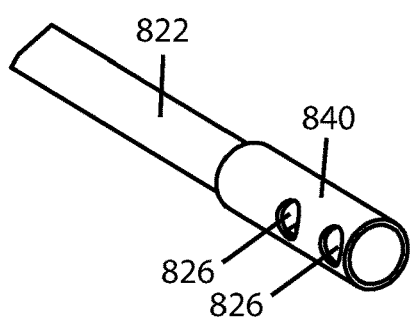
Figure 13H:
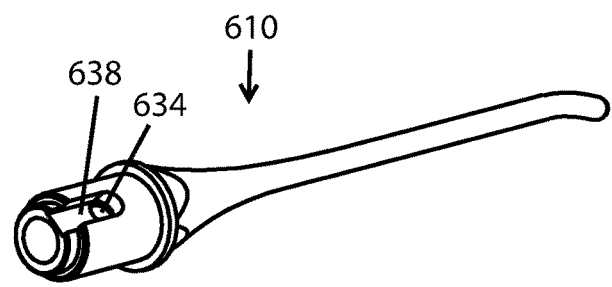
Figure 14A:
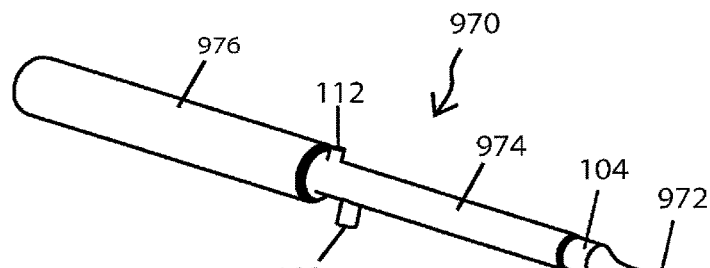
FIGS. 14A to 14D correspond to different perspective, detail and sectional views of one implementation of the flow regulator system of the present invention in an irrigation/aspiration surgical handpiece.
Figure 14B:
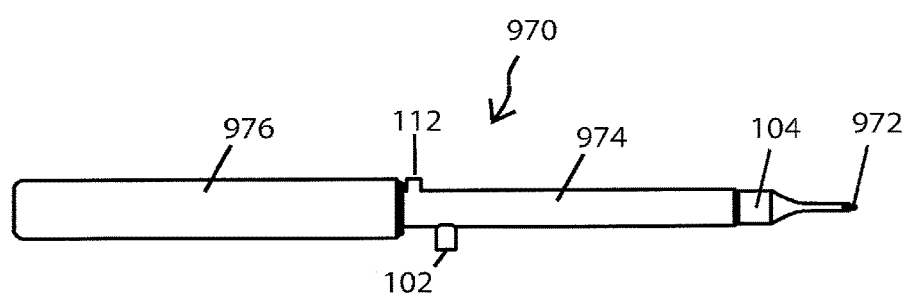
Figure 14C:
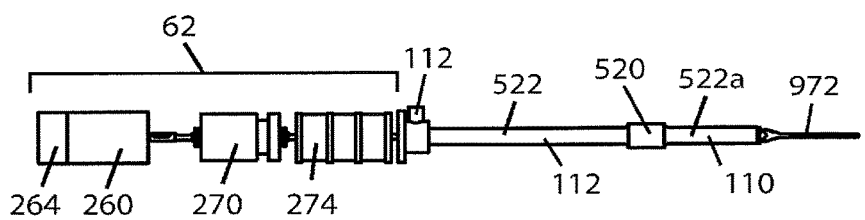
Figure 14D:
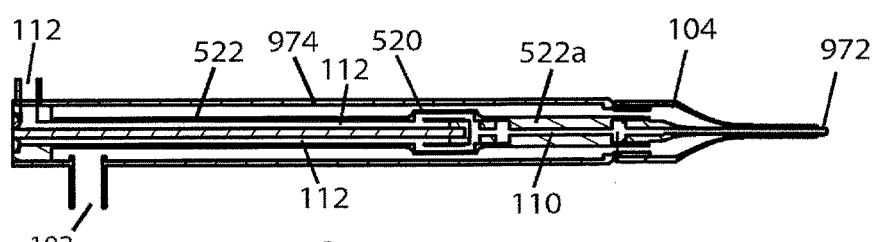

Depicted in FIGS. 13A to 13F is a handpiece 800 with an embodiment of the cyclic aperture flow regulator system 60 of the present invention that has an actuator portion 62 composed by an oscillatory linear actuator. Handpiece 800 shown in FIG. 13B with enclosure 502 removed exposes linear actuator 270 as the single flow regulator actuator mechanism. Linear actuator 270 is preferable a linear actuator. An "in-tube" valve portion 820 accommodates an oscillating valve in-tube piston 824 inside valve chamber 292. Shaft 822 can be configured to be rotationally stable having a single degree of freedom to coaxially displace inside tube 522 without rotation. Rotational stability of shaft 822 with attached in-tube piston 824 can contribute to the alignment between in-tube piston 824 and chamber 292. In-tube piston 824 can further incorporate a piston ring 828 for improved minimize leakage. At least one piston window 826 is arranged in a way that when shaft 822 is in an axial centered position no overlap exists between window 826 and the entrance of fluid passages 172 and 174. In this position the cross sectional area of aperture 200 is substantially reduced limiting or eventually cancelling flow. Operation of actuator 270 produces oscillation of the shaft of linear actuator 270 that transmits axial vibratory motion to in-tube piston 824 in a way that window 826 overlaps with the entrance of passages 172 and 174 in an alternating manner. This action produces cycles of variation of the cross-sectional area of aperture 200 (200a+200b) including a transition through the center position where the cross-sectional area of fluid aperture 200 is substantially reduced or closed. The frequency of the cycles of oscillation of in-tube piston 824 is determined by controller 132 driving actuator 270 to operate at a frequency sufficiently high to produce a substantially steady flow through surgical probe 80. Shown in FIG. 13C is a slice detail view from FIG. 13B showing a snapshot representation of in-tube piston 824 with windows 826 located in such position that a partial aperture 200 is conformed. Increasing the vibratory amplitude of in-tube piston 824 increases the RMS value of the cross-sectional area of aperture 200 increasing flow for a given vacuum in fluid path 112. Amplitude of vibration can be monitored using linear motion sensor 274 connected to controller 132. As with the preferred embodiment, this oscillatory version of the cyclic aperture flow regulator 60 can be implemented both with an "in-tube" valve portion 64 as depicted in FIGS. 13A to 13F or with an "in-probe" valve portion. FIG. 13G illustrates an in-valve piston 840 designed to match with a surgical probe 610 shown in FIG. 13H for "in probe" oscillatory operation. Surgical probe 610 is designed with a matching valve chamber to operatively receive in-valve piston 840. Fluid passages 634 and outflow channels 638 from probe 610 work in cooperation with windows 826 of in-valve piston 840 from FIG. 13G to complete the valve portion 64.

Stand-Alone Flow Regulator System Embodiment:

The cyclic aperture flow regulator system described in the preferred embodiment has an actuator portion 62 with sensors and actuators driven by a flow regulator controller 132 disposed in surgical console 150. Although this mode of operation allows the integration of multiple variables to improve system operation it is not a strict requirement for the implementation of this invention. Controller 132 including a processor and data storage memory can be incorporated in the same unit containing actuator portion 62 eventually requiring only external power such as a DC supply to operate in standalone mode. A user interface such as a foot pedal 152 can directly connect to this standalone flow regulator system unit for an operator to command operation. The unit can further incorporate a vacuum sensor 140 in fluid connection with second fluid path 112 and disposed for example in the valve portion 64 of the flow regulator system 60 and connected to controller 132 for improved control of operation. The flow regulator system 60 can operate independent of a surgical handpiece and can be disposed in-line in the aspiration path between a surgical handpiece and a vacuum source.

The cyclic flow regulator system of the present invention allows stable aspiration of fluid and tissue fragments from a body cavity such as the interior of an eye using high vacuum with adjustable flow rate. In this way surgical procedures can be performed faster, safer and require less auxiliary lens disrupting energy such as ultrasound or LASER.

The reader will see that the Cyclic Aperture Modulation Flow Regulator System here described allows to perform more efficient and safer surgical procedures by controlling flow and increasing the range of safe use of vacuum inside surgical aspiration lines. While the provided description contains many specificities, these should not be construed as limitations on the scope, but rather as an exemplification of several embodiments thereof. Many other variations are possible. The system has been primarily conceived for ocular surgery, and more particularly for lens removing surgeries such as cataract and refractive lensectomy procedures. Other surgical procedures where fluid and tissue fragments need to be removed through a surgical probe can benefit from the practice of the present invention such as for example, endoscopic joint surgeries. Design can widely vary. For example single or multiple apertures inside the valve chamber can be used. A diversity of shapes can be used for the entrance of the fluid passages that participate to conform the variable fluid apertures. Different numbers and shapes for fluid windows, ports and lids can be incorporated. Fluidic channels that participate in valve configuration can be closed or open and in such case being completed by neighboring parts. Different kinds of linear and rotary motors can be used. Different kinds of motion sensors can be used, all this without departing from the scope of the present invention. Accordingly, the scope should be determined not by the embodiment(s) illustrated, but by the appended claims and their legal equivalents.

The invention claimed is:
1. A cyclic aperture flow regulator system comprising:
a cyclic aperture flow regulator valve portion having a fluid passage with adjustable cross-sectional area, the fluid passage located in a fluid path connecting an aspiration opening of a surgical probe with a vacuum source, the cyclic aperture flow regulator valve portion comprising a valve rotor disposed in a valve chamber, the valve rotor capable of 360 degree rotation about an axis of rotation, the valve rotor disposed in the valve chamber such that the valve rotor is capable of translation in a direction parallel to the axis of rotation;
a cyclic aperture flow regulator actuator portion coupled to the cyclic aperture flow regulator valve portion, the cyclic aperture flow regulator actuator portion operable to modify a cross-sectional area of the fluid passage; and
a cyclic aperture flow regulator controller providing a cyclic command to the cyclic aperture flow regulator actuator portion to cause the valve rotor to continuously rotate through 360 degrees at a speed of greater than 2000 revolutions per minute so as to cause a plurality of cycles of variation of the cross-sectional area of the fluid passage, each of the plurality of cycles including at least one segment where the cross-sectional area of the fluid passage is substantially reduced or closed, the plurality of cycles occurring at a frequency sufficiently high to produce a flow that is substantially steady at the aspiration opening.

2. The system of claim 1 wherein a root means square value of the cross-sectional area of the fluid passage is user-adjustable.

3. The system of claim 1 wherein the valve rotor further comprises:
a rotor lid configured to rotate at the fluid passage, the rotor lid configured to at least partially occlude the fluid passage.

4. The system of claim 1 further comprising:
a linear actuator shaft operable to axially displace the valve rotor while the valve rotor is being rotated.

5. The system of claim 1 wherein the cyclic aperture flow regulator valve portion is incorporated into an aspiration fluid path of a handpiece.

6. The system of claim 1 wherein the cyclic aperture flow regulator actuator portion further comprises at least one of: a linear actuator and a rotary motor.

7. The system of claim 1 wherein the cyclic aperture flow regulator actuator portion further comprises:
a rotary position sensor.

8. The system of claim 1 wherein the cyclic aperture flow regulator actuator portion further comprises:
an axial position sensor.

9. A cyclic aperture flow regulator system comprising:
a cyclic aperture flow regulator valve portion comprising a valve rotor coupled to a rotor lid, the rotor lid continuously rotating 360 degrees inside a valve chamber about an axis of rotation, the rotor lid translating parallel to the axis of rotation,
a fluid passage with adjustable cross-sectional area, the fluid passage located in a fluid path connecting an aspiration opening of a surgical probe with a vacuum source, the fluid passage passing through the valve chamber;
a cyclic aperture flow regulator actuator portion coupled to the cyclic aperture flow regulator valve portion, the cyclic aperture flow regulator actuator portion comprising a rotary motor and a linear actuator, the cyclic aperture flow regulator actuator portion operable to rotate and translate the valve rotor to modify a cross-sectional area of the fluid passage; and
a cyclic aperture flow regulator controller providing a cyclic command to the cyclic aperture flow regulator actuator portion to cause cycles of variation of the cross-sectional area of the fluid passage, each of the cycles including at least one segment where the cross-sectional area of the fluid passage is substantially reduced or closed, the cycles occurring at a speed of greater than 2000 revolutions per minute so as to produce a flow that is substantially steady at the aspiration opening.

10. The system of claim 9 wherein a root means square value of the cross-sectional area of the fluid passage is user-adjustable.

11. The system of claim 9 wherein the valve rotor is slidably disposed inside the valve chamber.

12. The system of claim 11 wherein the rotor lid is configured to rotate at the fluid passage, the rotor lid configured to at least partially occlude the fluid passage.

13. The system of claim 11 further comprising:
a linear actuator shaft coupled to the valve rotor.

14. The system of claim 9 wherein the cycle aperture flow regulator valve portion is incorporated into an aspiration fluid path of a handpiece.

15. The system of claim 9 wherein the cyclic aperture flow regulator actuator portion further comprises:
a rotary position sensor; and
an axial position sensor.

16. The system of claim 9 wherein the rotary motor rotates the valve rotor and rotor lid to at least partially occlude the fluid passage periodically and the linear actuator moves the valve rotor to adjust a root means square value of the cross-sectional area of the fluid passage.

* * * * *